(12) United States Patent
Wegener et al.

(10) Patent No.: US 10,274,495 B2
(45) Date of Patent: Apr. 30, 2019

(54) SYSTEM AND METHOD FOR SEPARATING CELLS INCORPORATING MAGNETIC SEPARATION

(71) Applicant: Fenwal, Inc., Lake Zurich, IL (US)

(72) Inventors: Christopher J. Wegener, Libertyville, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 177 days.

(21) Appl. No.: 15/498,965

(22) Filed: Apr. 27, 2017

(65) Prior Publication Data
US 2018/0172685 A1    Jun. 21, 2018

Related U.S. Application Data

(60) Provisional application No. 62/437,267, filed on Dec. 21, 2016.

(51) Int. Cl.
*G01N 33/543* (2006.01)
*G01N 33/569* (2006.01)
(Continued)

(52) U.S. Cl.
CPC ..... *G01N 33/56972* (2013.01); *A61M 1/0281* (2013.01); *A61M 1/265* (2014.02);
(Continued)

(58) Field of Classification Search
USPC ......... 210/321.68, 651, 321.87, 650, 321.67, 210/497
See application file for complete search history.

(56) References Cited

U.S. PATENT DOCUMENTS 4,710,472 A * 12/1987 Saur ..................... B03C 1/01
209/215
5,053,121 A   10/1991 Schoendorfer et al.
(Continued)

FOREIGN PATENT DOCUMENTS

WO    WO 99/34848    7/1999
WO    WO 01/45830    6/2001
(Continued)

OTHER PUBLICATIONS

GE Healthcare Life Sciences, WAVE Bioreactor™ 2/10 system, 6 pages (Aug. 2012).
(Continued)

*Primary Examiner* — Erik B Crawford
(74) *Attorney, Agent, or Firm* — Cook Alex Ltd.

(57) ABSTRACT

A cell processing system includes a first processor connectable to a source container filled with a biological fluid, a second processor, and a controller coupled to the processors. The first processor includes a separator configured to separate the biological fluid into at least two streams of material, and a first container configured to receive one of the streams. The second processor includes a magnetic separator configured to select target cells, the target cells being associated with magnetic particles, a second, pass-through container associated with the magnetic separator, the second container connected at a first end to the first container, and a third container connected to a second end of the pass-through container. One of the processors includes at least one pump configured to transfer material between the separator and the first container, and between the first container and the second container.

8 Claims, 18 Drawing Sheets

(51) Int. Cl.
  *C12M 1/00* (2006.01)
  *C12M 1/36* (2006.01)
  *A61M 1/02* (2006.01)
  *A61M 1/34* (2006.01)
  *A61M 1/26* (2006.01)
  *A61M 1/36* (2006.01)

(52) U.S. Cl.
  CPC .......... *A61M 1/3496* (2013.01); *A61M 1/362* (2014.02); *A61M 1/3618* (2014.02); *C12M 29/04* (2013.01); *C12M 29/14* (2013.01); *C12M 41/48* (2013.01); *C12M 47/04* (2013.01); *G01N 33/54326* (2013.01); *G01N 33/54366* (2013.01)

(56) References Cited

U.S. PATENT DOCUMENTS

| | | | |
|---|---|---|---|
| 5,194,145 | A | 3/1993 | Schoendorfer |
| 5,536,475 | A * | 7/1996 | Moubayed ............ A61K 35/16 209/217 |
| 5,647,985 | A | 7/1997 | Ung-Chhun et al. |
| 5,738,792 | A | 4/1998 | Schoendorfer |
| 5,762,791 | A | 6/1998 | Deniega et al. |
| 5,972,217 | A | 10/1999 | Ung-Chhun et al. |
| 6,143,577 | A | 11/2000 | Bisconte |
| 6,251,284 | B1 | 6/2001 | Bischof et al. |
| 6,251,295 | B1 | 6/2001 | Johnson |
| 6,358,474 | B1 | 3/2002 | Dobler et al. |
| 6,423,023 | B1 | 7/2002 | Chang et al. |
| 6,497,821 | B1 | 12/2002 | Bellamy, Jr. et al. |
| 6,527,957 | B1 | 3/2003 | Deniega et al. |
| 6,706,008 | B2 | 3/2004 | Vishnoi et al. |
| 6,808,503 | B2 | 10/2004 | Farrell et al. |
| 6,863,821 | B2 | 3/2005 | Moriarty et al. |
| 6,960,178 | B2 | 11/2005 | Chang et al. |
| 6,969,367 | B2 | 11/2005 | Tu et al. |
| 6,994,781 | B2 | 2/2006 | Cork et al. |
| 7,364,921 | B1 | 4/2008 | Sciorra et al. |
| 7,390,484 | B2 | 6/2008 | Fraser et al. |
| 7,442,303 | B2 | 10/2008 | Jacobson |
| 7,470,245 | B2 | 12/2008 | Tu et al. |
| 7,514,075 | B2 | 4/2009 | Hedrick et al. |
| 7,585,670 | B2 | 9/2009 | Hedrick et al. |
| 7,771,716 | B2 | 8/2010 | Hedrick et al. |
| 8,105,580 | B2 | 1/2012 | Fraser et al. |
| 8,137,903 | B2 | 3/2012 | Kaufman et al. |
| 8,404,229 | B2 | 3/2013 | Fraser et al. |
| 8,481,336 | B2 | 7/2013 | Earhart et al. |
| 8,637,004 | B2 | 1/2014 | Danilkovich et al. |
| 8,727,132 | B2 | 5/2014 | Miltenyi et al. |
| 8,747,290 | B2 | 6/2014 | Miltenyi et al. |
| 8,808,978 | B2 | 8/2014 | Pages et al. |
| 8,951,782 | B2 | 2/2015 | Chang et al. |
| 9,217,131 | B2 | 12/2015 | Lamish et al. |
| 9,452,254 | B2 | 9/2016 | Kimura et al. |
| 9,511,094 | B2 | 12/2016 | Fraser et al. |
| 9,597,395 | B2 | 3/2017 | Fraser et al. |
| 2005/0048035 | A1 | 3/2005 | Fraser et al. |
| 2005/0048036 | A1 | 3/2005 | Hedrick et al. |
| 2010/0006509 | A1 | 1/2010 | Homes |
| 2010/0112695 | A1 | 5/2010 | Min |
| 2010/0112696 | A1 | 5/2010 | Min |
| 2012/0055854 | A1 | 3/2012 | Tibbe |
| 2012/0132593 | A1 | 5/2012 | Murthy et al. |
| 2013/0017538 | A1 | 1/2013 | Ionescu-Zanetti et al. |
| 2013/0092630 | A1 | 4/2013 | Wegener |
| 2015/0118728 | A1 | 4/2015 | Rahman et al. |
| 2016/0113967 | A1 | 4/2016 | Hedrick et al. |
| 2016/0244714 | A1 | 8/2016 | Spuhler et al. |
| 2016/0355777 | A1 | 12/2016 | Fachin et al. |
| 2017/0262601 | A1 | 9/2017 | Binninger et al. |
| 2017/0268037 | A1 | 9/2017 | Ionescu-Zanetti et al. |
| 2017/0313968 | A1 | 11/2017 | Wegener et al. |
| 2017/0315121 | A1 | 11/2017 | Wegener et al. |
| 2017/0340783 | A1 | 11/2017 | Wegener et al. |
| 2018/0015418 | A1 | 1/2018 | Binninger et al. |

FOREIGN PATENT DOCUMENTS

| | | |
|---|---|---|
| WO | WO 01/83002 A2 | 11/2001 |
| WO | WO 01/83002 A3 | 11/2001 |
| WO | WO 02/094351 A2 | 11/2002 |
| WO | WO 02/094351 A3 | 11/2002 |
| WO | WO 2010/075061 A2 | 7/2010 |
| WO | WO 2010/075061 A3 | 7/2010 |
| WO | WO 2012/125457 | 9/2012 |
| WO | WO 2012/125470 | 9/2012 |

OTHER PUBLICATIONS

Hollyman et al., Manufacturing Validation of Biologically Functional T Cells Targeted to CD19 Antigen for Autologous Adoptive Cell Therapy, Journal of Immunotherapy, vol. 32, No. 2, 169-180 (Feb.-Mar. 2009).

Levine et al., Large-Scale Production of CD4 + T Cells from HIV-1-Infected Donors After CD3/CD28 Costimulation, Journal of Hematotherapy 7:437-448 (1998).

ThermoFisher Scientific, DynaMag™ CTS™ Magnet, User Guide, 28 pages (May 25, 2015).

Thompson et al., A Phase I Trial of CD3/CD28-activated T Cells (Xcellerated T Cells) and Interleukin-2 in Patients with Metastatic Renal Cell Carcinoma, Clinical Cancer Research, vol. 9, pp. 3562-3570 (Sep. 1, 2003).

White et al., Intravenous Safety Study in Rats Given Paramagnetic, Polystyrene Beads with Covalently Bound Sheep Anti-Mouse Immunoglobulin G (IgG), Journal of the American College of Toxicology 14(4):251-265 (1995).

European Patent Office, Extended European Search Report, counterpart EP Appl. No. 17168415 (dated Nov. 16, 2017).

* cited by examiner

SYSTEM AND METHOD FOR SEPARATING CELLS INCORPORATING MAGNETIC SEPARATION

CROSS-REFERENCE TO RELATED APPLICATIONS

This application claims the benefit of U.S. Provisional Application No. 62/437,267, filed Dec. 21, 2016, which is hereby incorporated herein by reference.

TECHNICAL FIELD

The present disclosure is generally directed to a system and method for separation of a cell of interest or a target cell from a collection of cells, and in particular a system and method for separation of the target cell using a first separator to remove certain cells from the solution, and a second magnetic separator to separate the target cells from other cells remaining in the solution.

BACKGROUND

The processing of biological fluid such as blood or blood components typically involves using a reusable processing apparatus ("hardware") and a disposable fluid circuit adapted for mounting or other association with the reusable apparatus. The fluid circuit typically includes container such as plastic bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

SUMMARY

In one aspect, a cell processing system includes a first processor connectable to a source container filled with a biological fluid. The first processor includes a separator configured to separate the biological fluid from the source container into at least two streams of material, and a first container configured to receive one of the at least two streams along a first fluid pathway. The system also includes a second processor connectable to the first container. The second processor includes a magnetic separator configured to select target cells, the target cells being associated with magnetic particles, a second, pass-through container associated with the magnetic separator, the second container connected at a first end to the first container along a second fluid pathway, and a third container connected to a second end of the pass-through container. One of the first processor and the second processor includes at least one pump configured to transfer material between the separator and the first container along the first fluid pathway, and between the first container and the second container along the second fluid pathway. The system also includes at least one controller coupled to the first processor and the second processor.

According to another aspect, a cell processing method includes separating a biological fluid into at least two streams, one of the streams including target cells, associating magnetic particles with the target cells, transporting the target cells with associated magnetic particles to a pass-through container via a port at a first end of the pass-through container, selecting the target cells in the pass-through container using a magnetic field, and transporting non-selected materials from the pass-through container via a port at a second end of the pass-through container opposite the first end.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Figure 1:
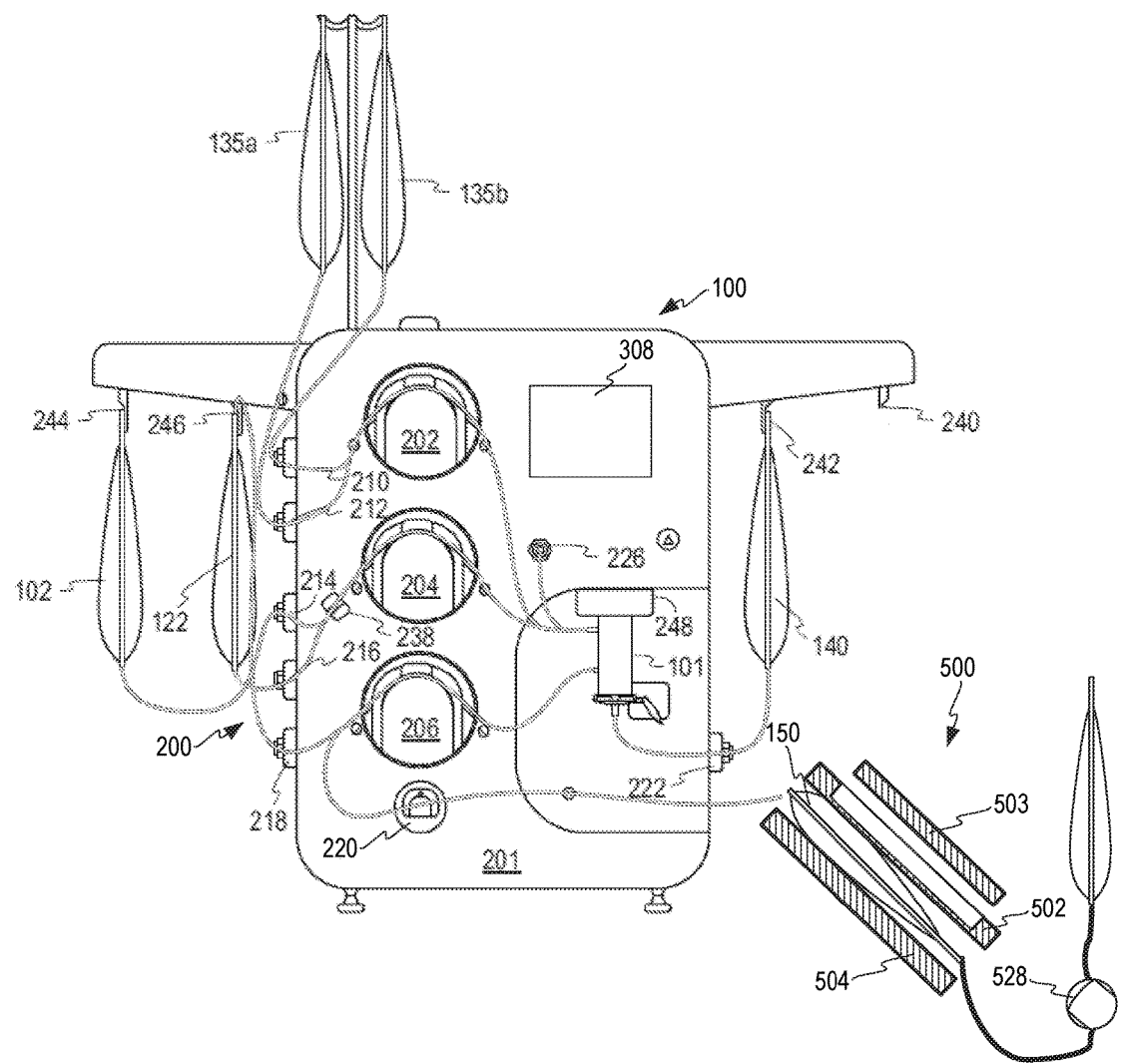
FIG. 1 is a frontal view of a reusable cell processing system with a disposable fluid circuit loaded thereon.
Figure 2:
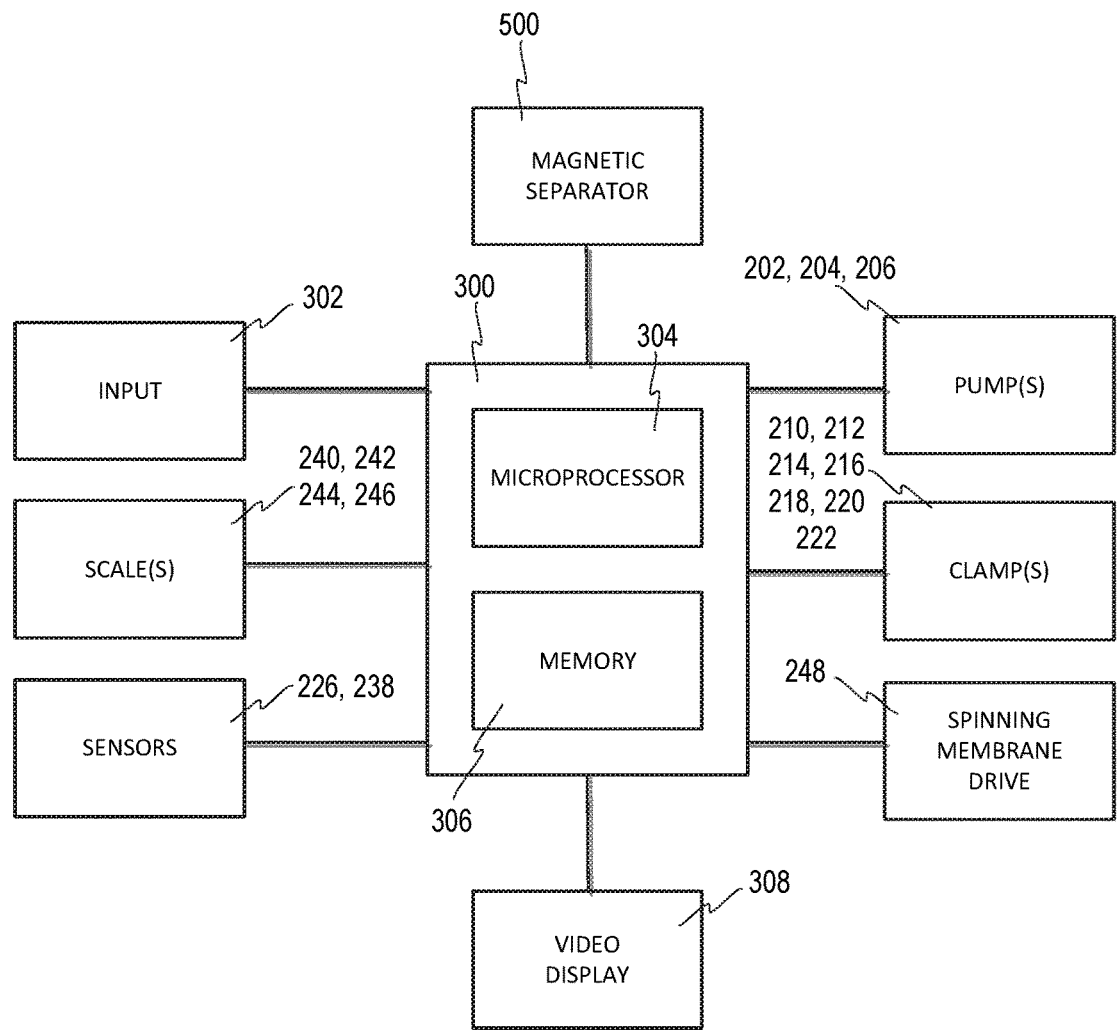
FIG. 2 is a schematic view of the control circuitry of the apparatus of FIG. 1.
Figure 6:
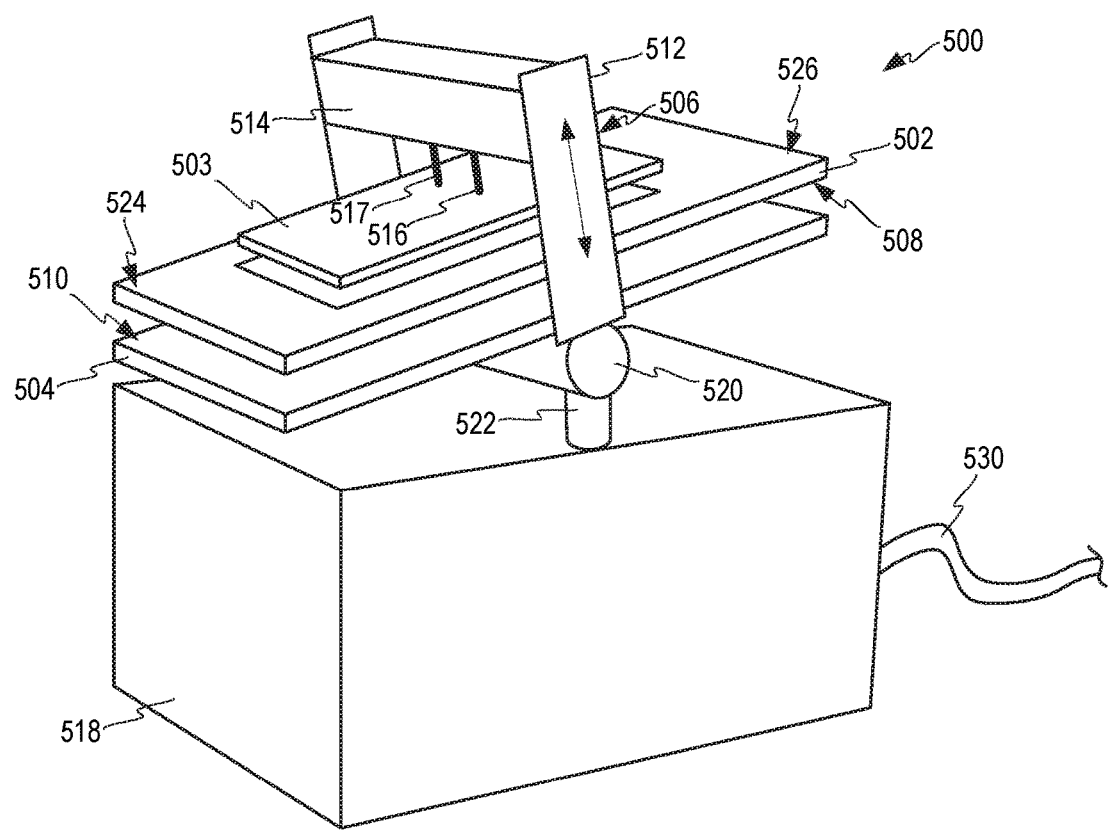
FIG. 6 is a perspective view of a reusable magnetic separation or selection apparatus.

As illustrated in FIGS. 1 and 2, a cell processing system includes a processor 100, 200 to receive a biological fluid to be processed, and a control unit (or controller) 300 coupled to the processor 100, 200, the controller 300 configured to operate the processor 100, 200 according to a procedure or process to produce or generate a product that may be disposed in a product container. According to the embodiments described herein, the cell processing system may be used in conjunction with a magnetic separator or selector 500, as illustrated generally in FIG. 1 and the details of an embodiment of which are illustrated in FIG. 6. The magnetic separator 500 may be included as part of the system to provide an additional selection of cells of interest or target cells, which target cells were initially separated from a biological fluid by the processor 100, 200.

Figure 3:
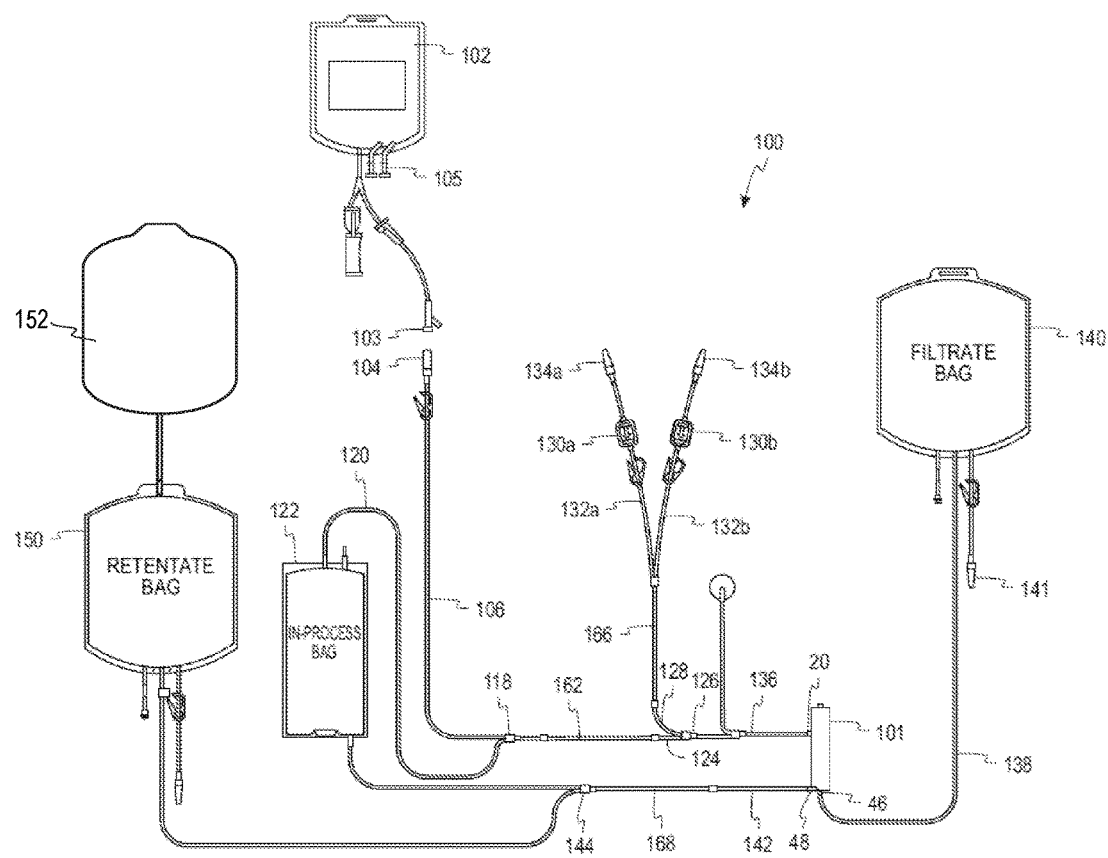
FIG. 3 is a schematic view of one embodiment of a disposable fluid circuit useful in the systems and methods described herein.
Figure 4:
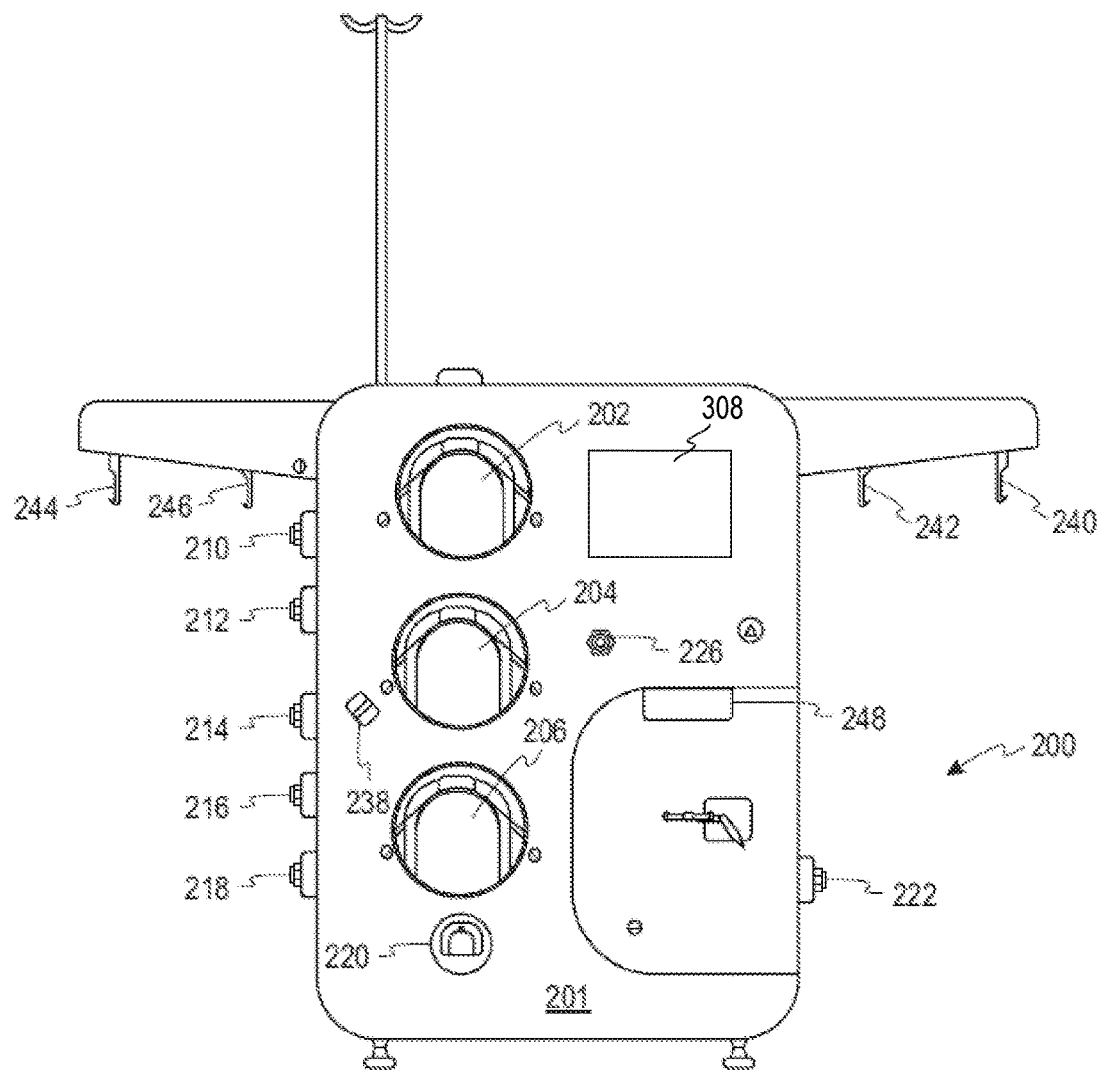
FIG. 4 is a frontal view of the reusable cell processing apparatus.

Starting with the processor, the illustrated embodiments of the processor may include a disposable processing fluid circuit 100 (see also FIG. 3) and reusable hardware 200 (see also FIG. 4). According to the illustrated embodiments in FIGS. 1 and 3, the disposable fluid circuit 100 may include a first separator in the form of a spinning membrane 101, at least one container 102, 122, 135a, 135b, 140, 150, 152 and tubing 106, 120, 128, 132a, 132b, 162, 166, 168, which tubing connects the spinning membrane 101 and the one or more containers 102, 122, 135a, 135b, 140, 150 and defines fluid pathways. As is also illustrated, the reusable hardware 200 may include at least one drive 248 to spin the spinning membrane 101, at least one scale 240, 242, 244, 246 to weigh the at least container 102, 122, 140 and contents thereof, and at least one pump 202, 204, 206 to receive the tubing 162, 166, 168 and pump fluid through the tubing 162, 166, 168 by peristaltic action, for example, although other types of pumps and pumping action may be used. The controller 300 may, according to the embodiments, include a programmable microprocessor 304, which microprocessor 304 may be coupled to the at least one input 302 and may be programmed to operate the processor according to a process.

Thus, the cell processing systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

The illustrated processing apparatus is typically capable of effecting the separation of a biological fluid that includes biological cells into two or more components or fractions. Thus, the reusable apparatus may generate conditions that allow for the separation of a biological fluid into selected components or fractions. One preferred machine for separating biological fluid into its constituent components or fractions uses a spinning porous membrane. An example of such machine is the Autopheresis C® sold by Fenwal, Inc. of Lake Zurich, Ill., which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which are also incorporated herein in their entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane-covered spinner having an interior collection system disposed within a stationary shell. While a detailed discussion of the separation device is beyond the scope of this application, the spinning membrane separation device is shown in FIGS. 6, 7(a)-7(b) of the reference cited and is discussed below in general terms. In another embodiment, the reusable apparatus may generate a centrifugal field to effect separation.

Turning now to FIG. 3, the systems described herein include at least one disposable fluid circuit 100 for use in the processing of biological fluid. While the circuits described herein may be used as stand-alone circuits, at least two or more disposable fluid circuits may be used in combination and in series for the separation, washing, volume reduction and/or other processing of a biological fluid. The circuit 100 may be a "closed" system or circuit, in which the interior of the system, e.g., the flow paths, container, etc., are not exposed or "opened" to the outside environment; the circuit 100 may be referred to as closed even where additional containers are attached to the circuit 100, for example before or during a procedure. Circuit 100 may include an integrated separation device, such as, but not limited to, the spinning membrane 101 described above. Circuit 100 may also include waste container 140, product container 150 and related waste container 152, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths or fluid pathways throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized poly(vinyl chloride). Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in a different and/or earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the CompoDock, available from Fresenius Kabi AG, the BioWelder, available from Sartorius AG, or the SCD IIB Tubing Welder, available from Terumo Medical Corporation. A second access port 105 may also be provided for extracting fluid from the source container 102 and/or introducing materials into the source container.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, e.g., saline, additive solution, buffer, etc. As one example, the wash fluid or medium may comprise a buffer comprising PBS, EDTA, HSA and/or saline. Tubings 132a, 132b may include in-line sterile barrier filters 130a, 130b for filtering any particulate from a fluid before it enters the flow path leading to second branched-connector 126 and ultimately separator 101. In one embodiment, the sterile barrier filters 130a, 130b may be 0.2 µm filters. The wash medium or fluid flows from the wash fluid source through tubing segments 132a, 132b where it is filtered by the sterile barrier filters 130a, 130b described above, and then passes through tubing 128 to the input of the branched-connector 126.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container 140 includes a further connection port 141 for sampling or withdrawing the waste from within the product container.

Separation device 101 preferably includes a second outlet 48 that is connected to tubing segment 142 for directing the desired biological cell/fluid product to the in-process container(s) 122 or the product container 150. To permit this, the other end of tubing segment 142 is connected to branched-connector 144, which may branch into and define a flow path to one or more in-process containers 122 and a flow path to a "final" product container 150. The product container 150 may also include a sampling assembly (not shown).

FIG. 4 shows the front panel 201 of reusable hardware processing apparatus 200, also referred to herein as "hardware". Apparatus 200 may be of compact size suitable for placement on a tabletop of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201, which pumps 202, 204, 206 may be bi-directional peristaltic pumps. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container 150, waste container 140, the source container 102 and the in-process container 122, respectively, typically may depend and be weighed. According to the present disclosure, the product container 150 is disposed instead in the magnetic selector 500, between plates or panels 502, 504 (see, e.g., FIG. 1) instead of depending from scale 240. The weights of the bags may be monitored by weight sensors and recorded during a washing or other procedure. From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
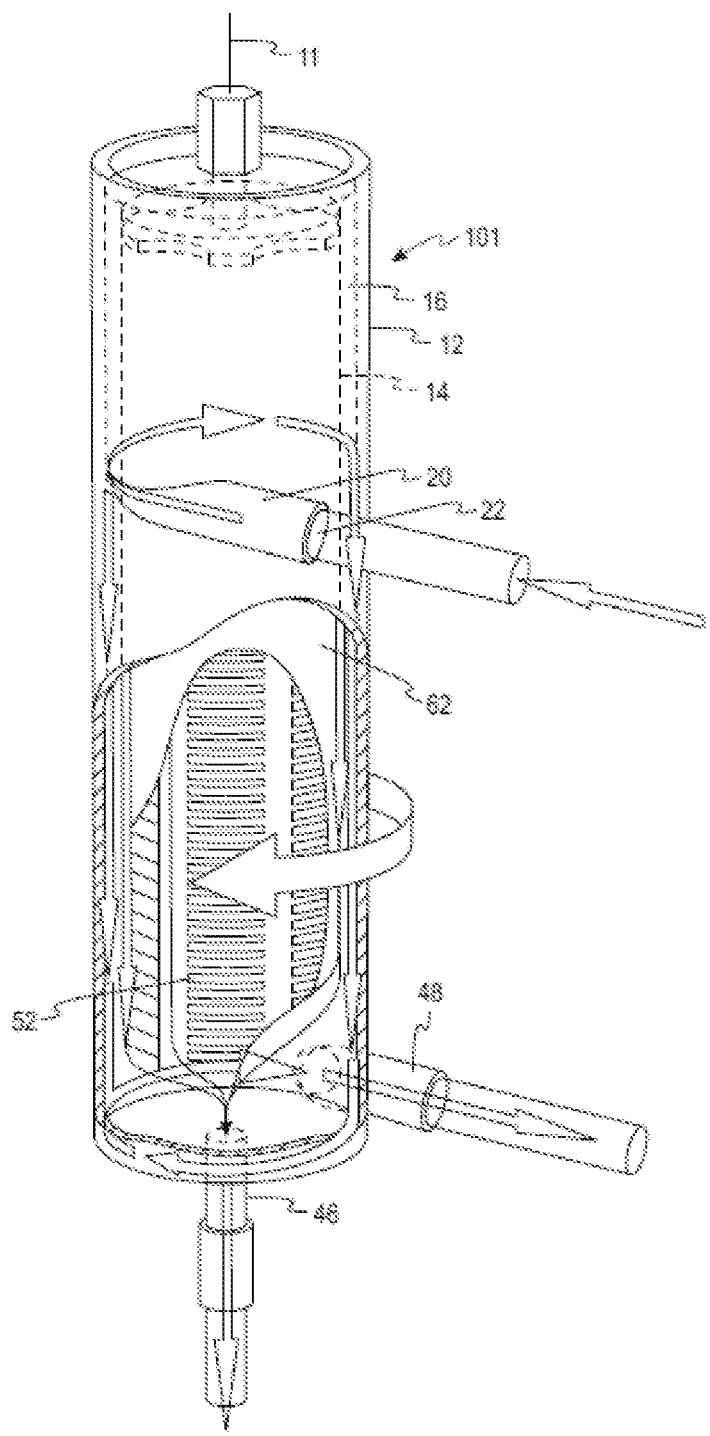
FIG. 5 is a perspective view of a separation/washing device using a spinning membrane.

Turning to FIG. 5, a spinning membrane separation device, generally designated 101, is shown. Such a device 101 may form part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. As illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48. Cylindrical housing 12 may be completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 30.0 microns (μm), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.8 μm and a thickness of approximately 150 μm or greater. Membranes of this type will typically retain all cellular components (e.g., red blood cells and white blood cells (or leukocytes)) and certain formed blood components, e.g., platelets (~2-4 μm). In another embodiment relevant to the process discussed below, the membrane may be made of a thin (approximately 10-50 μm thick) sheet of unsupported polycarbonate, for example, with a pore size of approximately 4.0 μm. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

As explained above, the illustrated embodiment of the cell processing system also includes an embodiment of a magnetic separator or selector 500, which is illustrated schematically in FIG. 1 (as plates 502, 504 and magnet 503) and in detail in FIG. 6. The magnetic separator 500 includes a first panel or plate 502 and a second, opposing panel or plate 504. According to the embodiments described herein, the first plate 502 comprises a magnet 503 (which may be a permanent magnet or an electromagnet), while the second plate 504 is non-magnetic. It will be recognized that according to other embodiments, the second plate 504 comprises a magnet and the first plate is non-magnetic. As such, the reference to the first and second plates 502, 504 relative to the magnet is intended to be non-limiting.

The plates 502, 504 are mounted on a frame 506 to permit at least one of the plates 502, 504 to translate relative to the other plate 502, 504 in the direction of the double-headed arrow in FIG. 6 between a first position where facing surfaces 508, 510 of the plates 502, 504 are close to each other (potentially, even abutting) and one or more second positions where the inner surfaces 508, 510 of the plates 502, 504 are spaced from each other (as illustrated). For example, the frame 506 may include one or more side pieces or legs 512 joined by a crosspiece 514, each of the legs 512 having a slot in which a tab or extension from the plate 502 is received to limit the motion of the plate 502 to a linear direction relative to the plate 504. The separator 500 may also include a linear actuator 516, which may be housed in the crosspiece 514 of the frame 506 and a portion of which is illustrated in FIG. 6, that is used to vary the spacing between opposing surfaces of the plates 502, 504 (the linear actuator 516 may depend through the magnet 503). As an alternative, the spacing may be varied using a mechanism that is manually activated (e.g., a fastener that secures the plates 502, 504 in a particular position relative to each other).

In a similar fashion, the magnet 503 is mounted on the frame 506 to permit the magnet 503 to translate relative to the plate 502 in the direction of the double-headed arrow in FIG. 6 between a first position where the magnet 503 is received within a recess formed in the plate 502 and a second position where the magnet 503 is spaced from the plate 502, and in particular the recess formed in the plate 502 (as illustrated). The separator 500 may also include a linear actuator 517, which also may be housed in the crosspiece 514 of the frame 506 and a portion of which is illustrated in FIG. 6, that is used to vary the spacing between the magnet 503 and the plate 502. As an alternative, the spacing may be varied using a mechanism that is manually activated (e.g., a fastener that secures the plate 502 and the magnet 503 in a particular position relative to each other).

A container 150 is intended to be associated with the separator 500, and in particular between the plates 502, 504. In the same fashion as the circuit 100 and apparatus 200 may be referred to as defining a first processor, the circuit 100 (or as much of the interconnected set as disposed in the separator 500) and the separator may be referred to as defining a second processor. Because it is intended for the container 150 to be disposed between the plates 502, 504, the plate 504 may be in the form of a bed, table or tray, and may have a boundary (such as in the form of a rim, lip or flange) that will assist in maintaining the container on the plate 504. According to certain embodiments, the plate 504 (and potentially the plate 502) may have a depression in which the container is received when the container is disposed between the plates 502, 504.

The frame 506 may be mounted on a base 518. According to the illustrated embodiment, the frame 506 may be attached to an axle 520 that is mounted on the base 518 on legs 522, for example. The frame 506 may pivot about the axle 520 relative to the base 518 to vary the elevation of a first end 524 of the plates 502, 504 relative to a second end 526 of the plates 502, 504. The pivoting movement of the frame 506 (and plates 502, 504) may be controlled using a motor or other actuator. The pivoting movement of the frame 506 may be controlled so as to permit the elevation of the first end 524 to be adjusted and maintained relative to the elevation of the second end 526 to maintain an incline (as illustrated in FIG. 6). Alternatively, the pivoting motion of the frame 506 may cause the elevation of the first and second ends 524, 526 of the plates 502, 504 to alternate back and forth in an oscillating motion, which may be useful in agitating the contents of a container that is disposed between the plates 502, 504 (e.g., container 140 as illustrated in FIG. 1).

The magnetic separator 500 may also include at least one clamp 528, as illustrated in FIG. 1 and FIGS. 8-29. The clamp 528 is used to open and close a fluid path between the container 150 and the container 152, the flow path between the containers 150, 152 permitting the container 150 to be operated as a flow-through container. When the clamp 528 is open, the fluid path between the container 150 and the container 152 is open, and when the clamp 528 is closed, the fluid path between the container 150 and the container 152 is closed. The clamp 528 may be mounted to the base 518 of the separator 500 according to one embodiment.

The operation of the actuators 516, 517, the motor or actuator used to vary the relative elevation of the ends 524, 526 of the plates 502, 504 (and thus the inclination of the plates 502, 504), and the clamp 528 may be controlled by a controller disposed in the base 518 of the magnetic separator 500 (which may be in the form of a microprocessor and memory, and/or other hard-wired circuitry—see also the description of the controller 300, below). Alternatively, the operation of the separator 500 may be controlled by the controller 300 of the apparatus 100. In either event, the separator 500 may include a cable 530 that is coupled to the apparatus 100. The cable 530 may be used to provide a one-way or two-way communication link between the apparatus 100 and the separator 500, and may also be used to provide power to the separator 500 according to certain embodiments.

Having thus described the processor, including disposable circuit 100 and reusable hardware 200, and the separator 500, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. As also mentioned above, the controller 300 may be coupled to the magnetic separator 500. It may also be possible that the controller 300 receives information from and provides commands to a given structure, such as one of the structures already mentioned (e.g., the magnetic separator 500). The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the afore-mentioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing of biological cells, such as leukocytes for subsequent therapeutic administration.

In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Similar self-calibration checks may be performed relative to the separator 500 when the operator activates the separator 500, or when the operator activates the apparatus 200. Apparatus 200 may then prompt the user to enter or modify process parameters using the input 302, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 300 prompts the operator to connect the biological fluid (e.g., 102 of FIG. 3) via a spike connector or sterile connection (e.g., 103, 104 of FIG. 3) and the wash medium (e.g., 135a, 135b of FIG. 3) via a spike connector (e.g., 134a, 134b of FIG. 3) or sterile welded. In one embodiment, the biological fluid/cells may be apheresis-collected leukocytes, and the wash medium may be a saline solution.

Once the operator confirms that the solutions are connected, the controller 300 primes the disposable set 100. In the embodiment discussed above, the set 100 may be primed with saline, although other biocompatible aqueous solutions may also be used. The controller 300 then commences processing the biological fluid/cells, which may have been recently obtained via apheresis (or leukapheresis), refrigerated overnight, etc. The biological fluid/cells is/are transferred from source container (e.g., 102 of FIG. 3) through the set to the spinning membrane separator 101 via the operation of one or more peristaltic pumps 202, 204 and 206. In a similar fashion, the wash medium may be delivered from its container (e.g., 135a, 135b of FIG. 3) through the set to the spinning membrane separator 101. The biological cells are collected in the in-process container (e.g., 122 of FIG. 3), while supernatant is separated and removed to waste container (e.g., 140 of FIG. 3). In regard to this portion of the method, the disclosure of U.S. Provisional Application 62/329,636 is also incorporated by reference herein in its entirety, and in particular the settings for the apparatus described in the disclosure and figures.

According to the present disclosure, a monoclonal antibody solution may be introduced to the solution in the in-process container 122, and incubated for a period of time to allow for interaction between the monoclonal antibodies in the solution and the target cells (which may be white blood cells of a particular phenotype, such as CD34+ peripheral blood stem cells, CD3+/CD28+ T-cell lymphocytes, and CD8+ plasma B-cells, which cells may also be referred to as target cells). The spinning membrane separator 101 may be used to mix the cells and then to wash the cells, removing any unbound monoclonal antibodies. In regard to this portion of the method, the disclosure of U.S. Provisional Application 62/329,636 is again incorporated by reference herein in its entirety, and in particular the settings for the apparatus described in the disclosure and figures.

At this point, a non-specific magnetic particle solution (e.g., a magnetic bead solution, such as ferrofluid (FF)) may be introduced to the suspension in the in-process container 122, incubated for a period of time to allow for interaction between the ferrofluid and the non-specific end of the monoclonal antibodies, mixed and (optionally) washed to remove any unbound ferrofluid. The target cells with associated magnetic particles may then be transferred to the container 150 that is disposed in magnetic separator 150.

The magnetic plate 502 may be actuated and/or positioned adjacent the container 150 to attract the magnetic particles, and in particular the magnetic particles associated with the target cells, to a particular portion of the container 150 (e.g., the upper section of the container 150 adjacent the plate 502 as illustrated in FIG. 1). The container 150 may then be agitated and the negative fractions removed. Additional fluid then may be added to the container to achieve a desired final volume, and the magnet may be disengaged and/or the plate 502 may be moved to relative to the plate 504 so that the plates 502, 504 are spaced (which may include reference to further spacing as well). Once the processing is completed, the controller prompts the operator to sample, seal and remove the product container 150.

Figure 7:
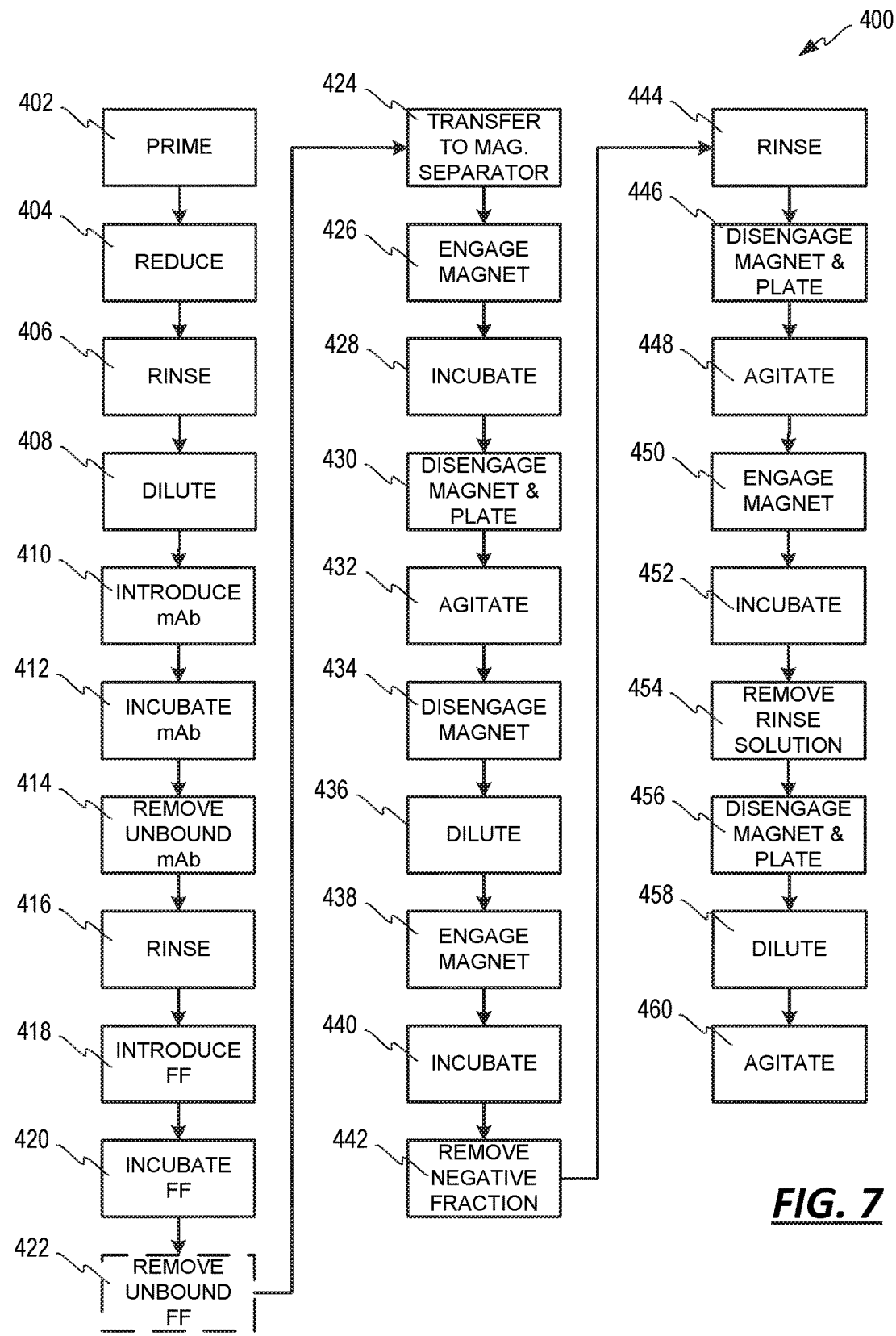
FIG. 7 is a flowchart of one embodiment of a method of operating a reusable cell processing apparatus with a disposable fluid circuit loaded thereon, such as is illustrated in FIG. 1, to process a biological fluid.
Figure 8:
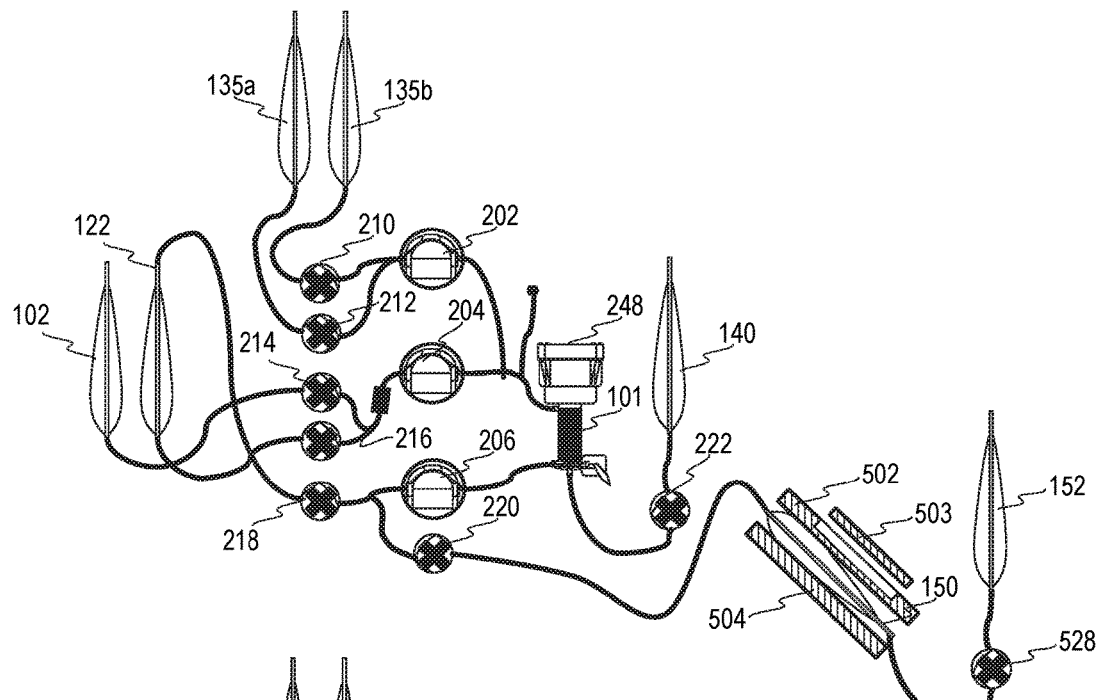
FIGS. 8-29 are schematic views of selected portions of the reusable cell processing apparatus, the reusable magnetic separation apparatus, and the disposable fluid circuit illustrating the movement of materials to various elements and along various fluid paths of the fluid circuit according to the method illustrated in the flowchart of FIG. 7.
Figure 9:
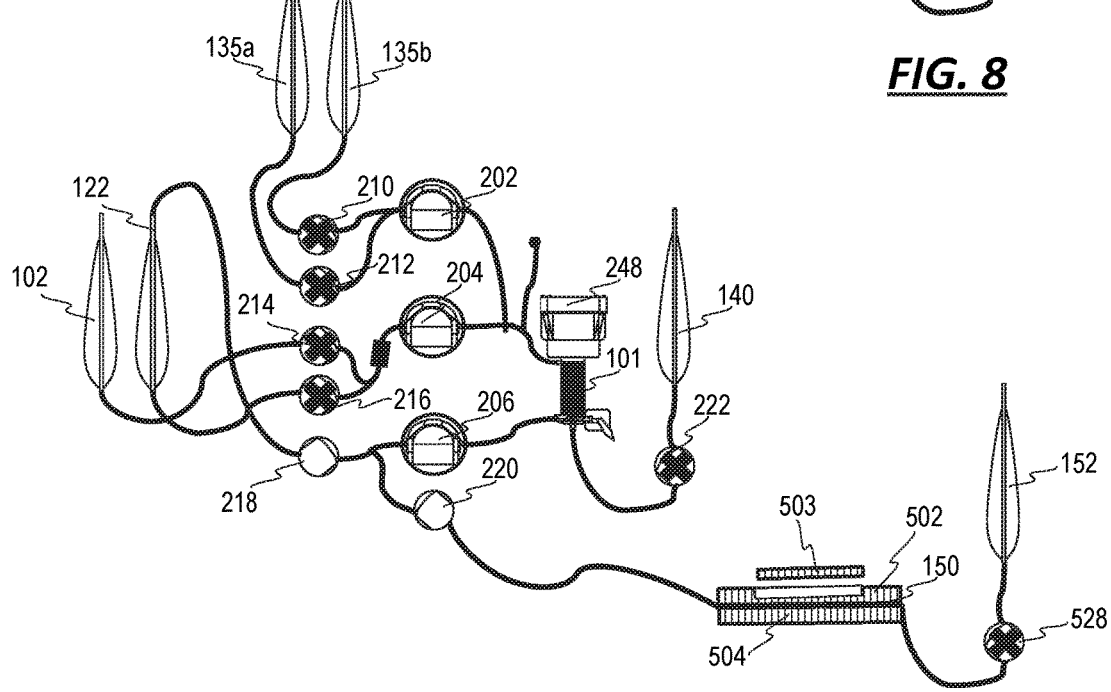
Figure 10:
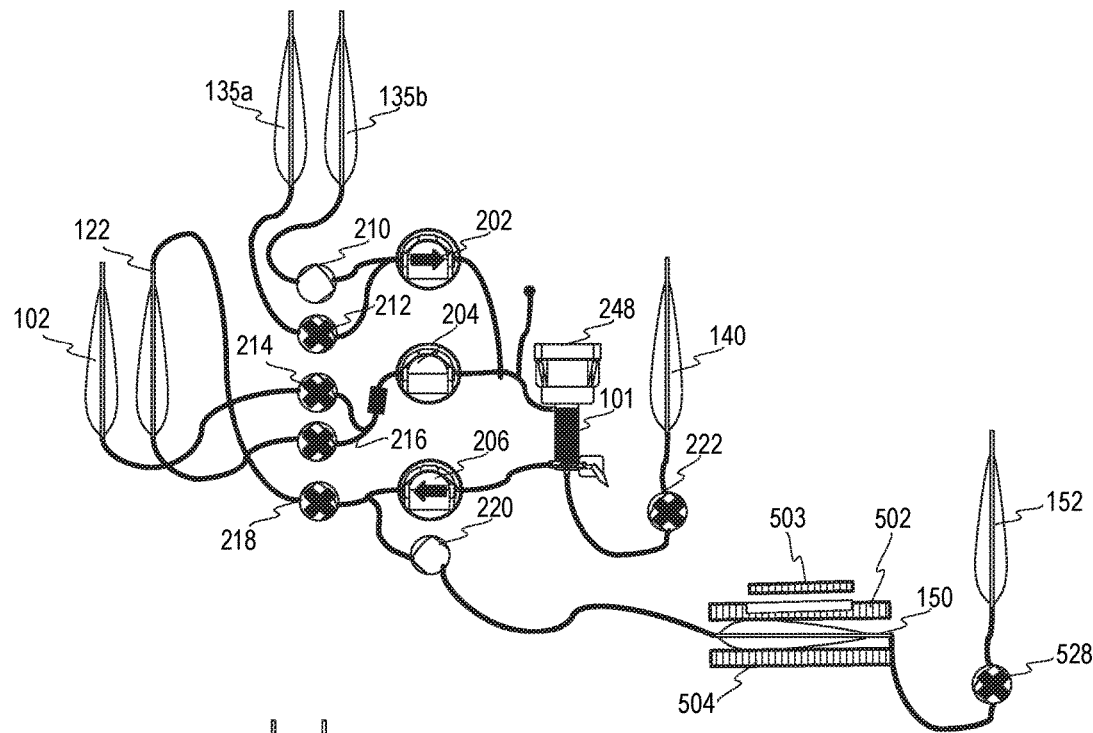
Figure 11:
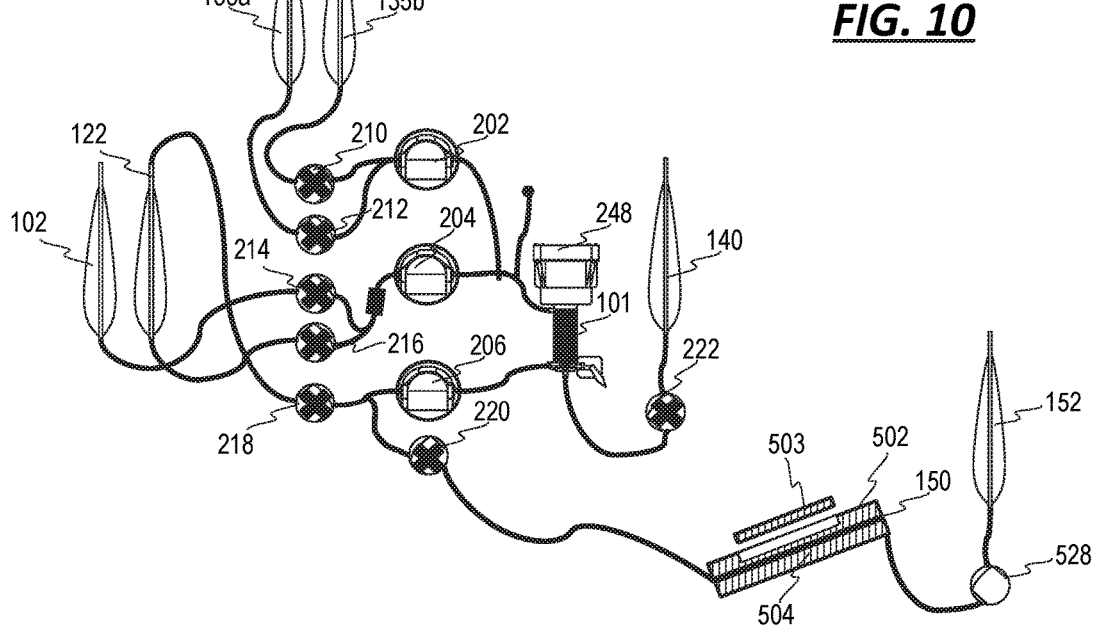
Figure 12:
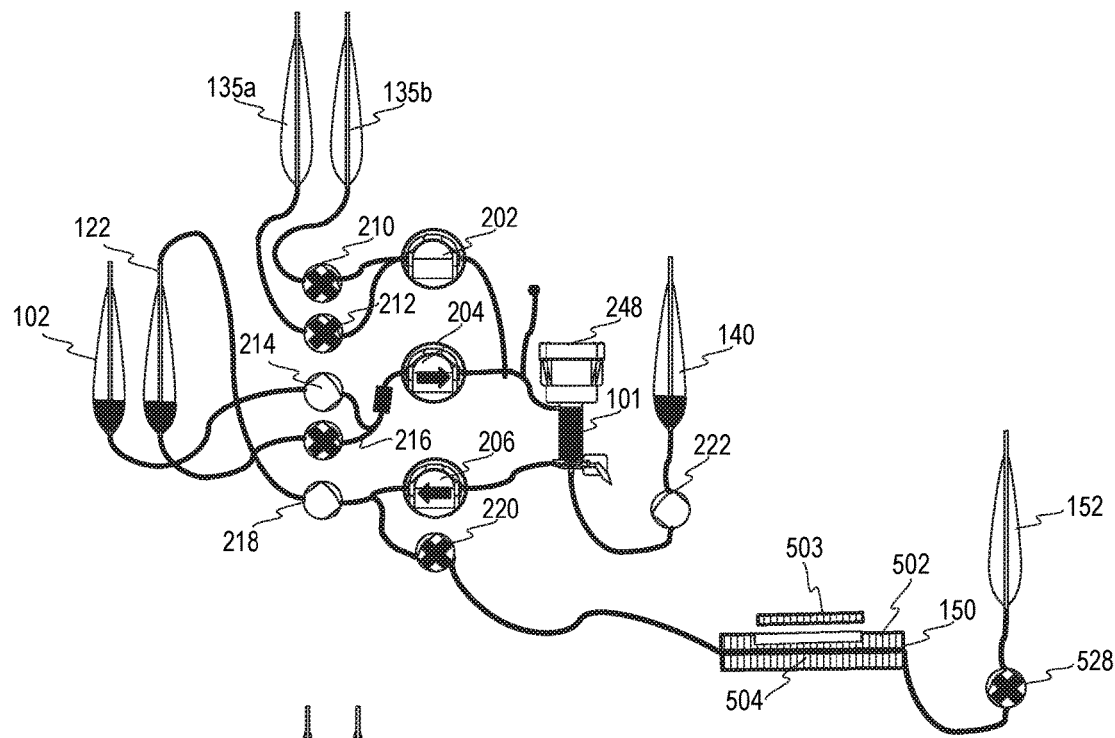
Figure 13:
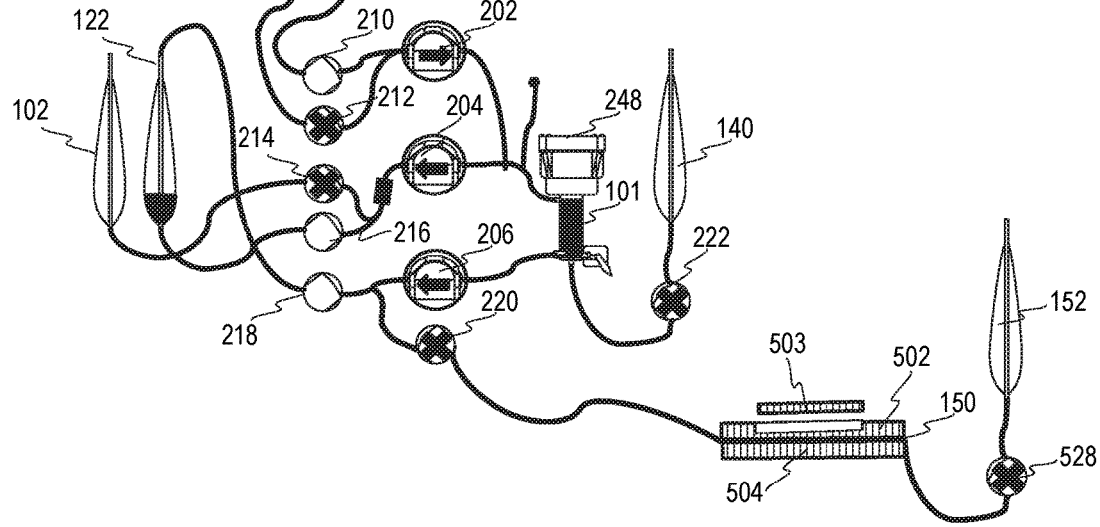
Figure 14:
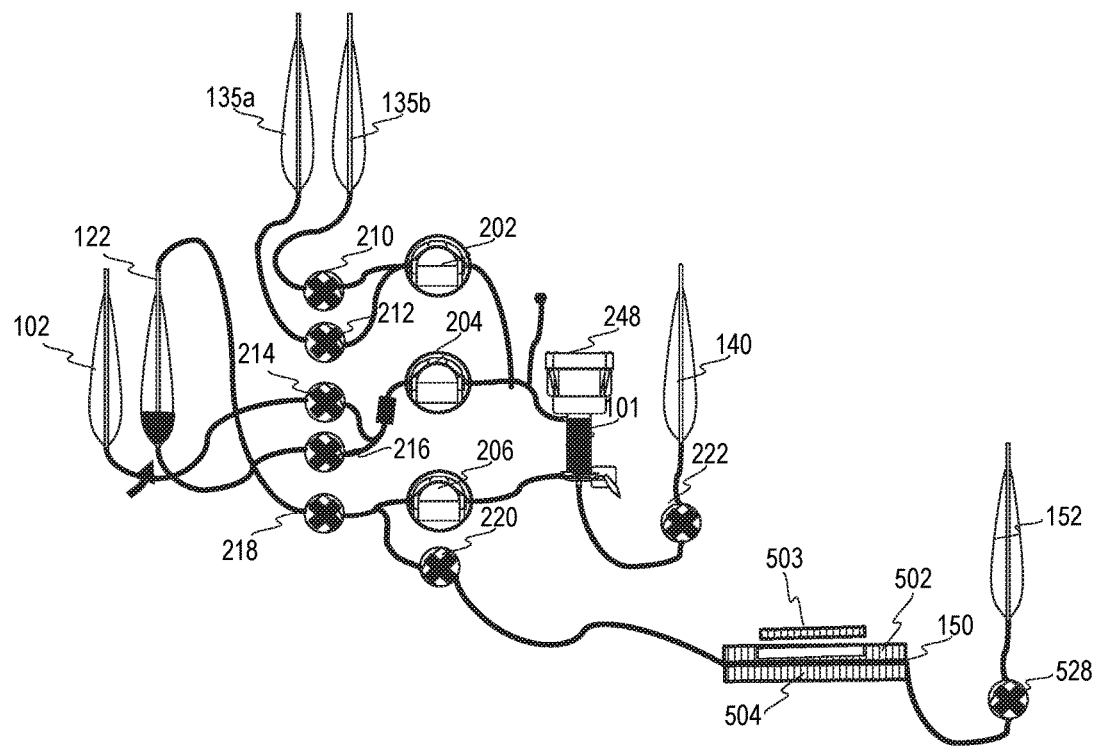
Figure 15:
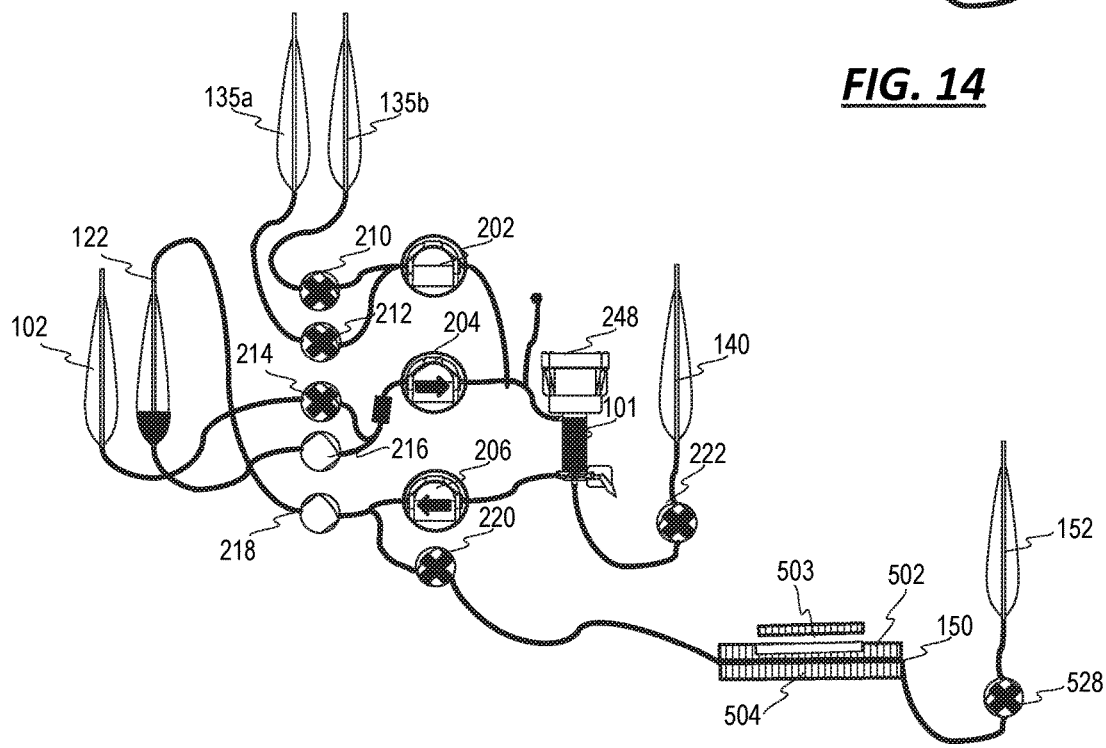
Figure 16:
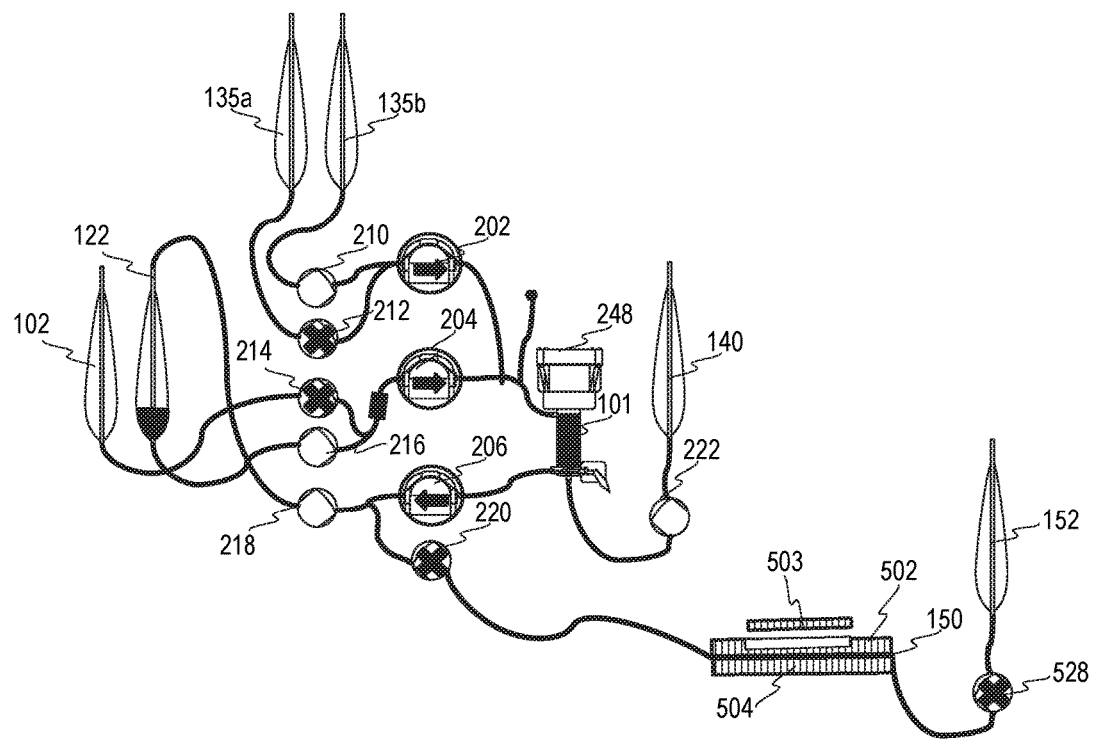
Figure 17:
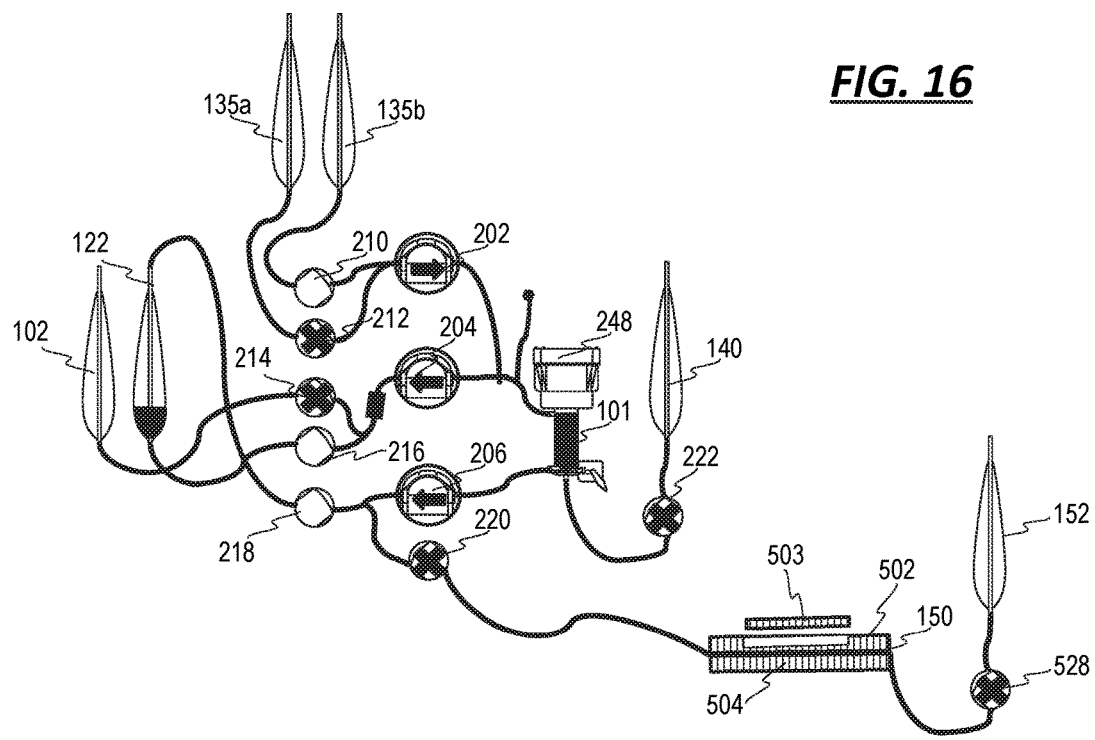
Figure 18:
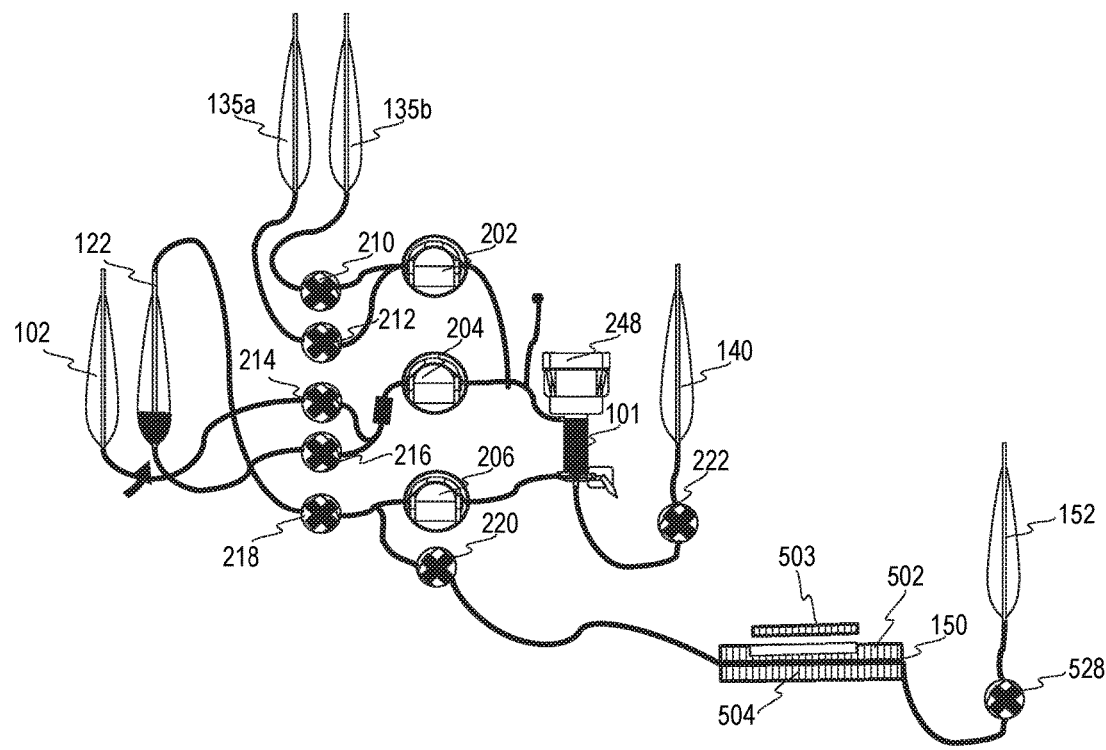
Figure 19:
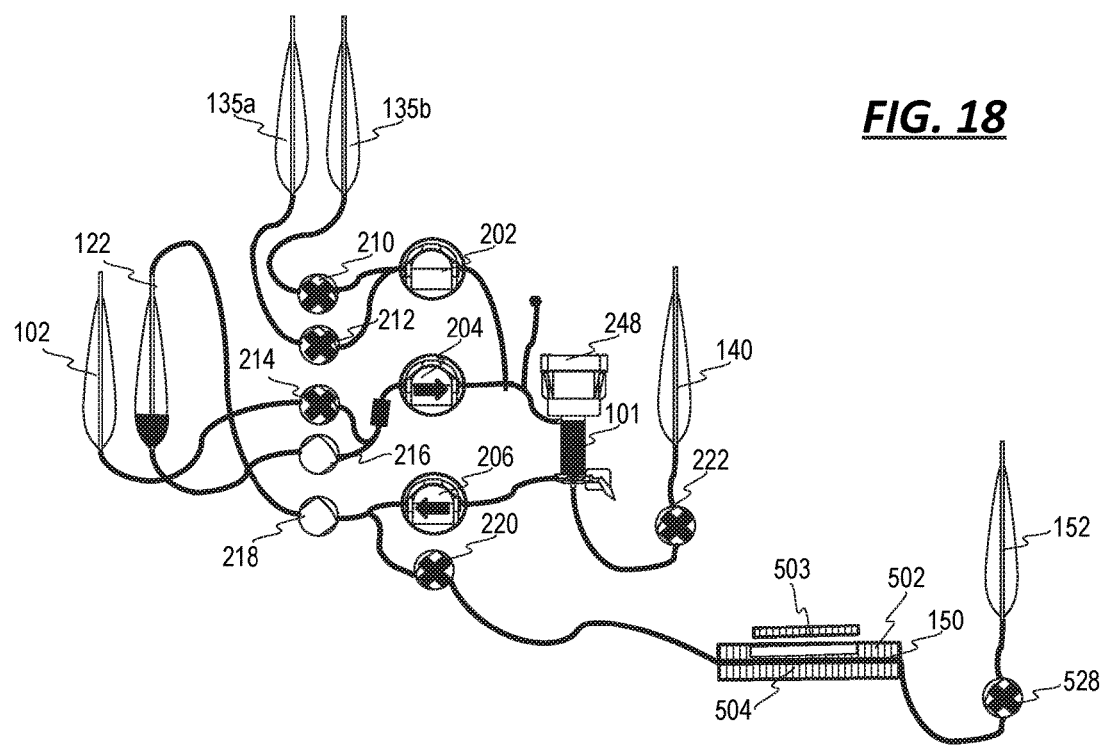
Figure 20:
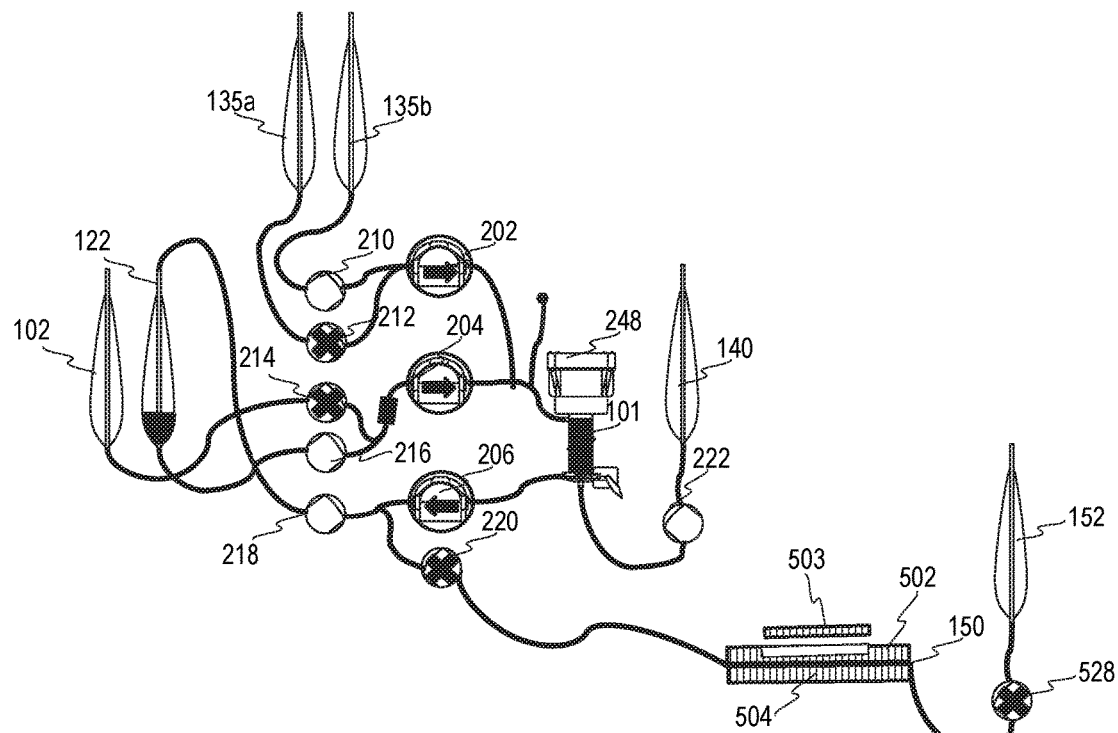
Figure 21:
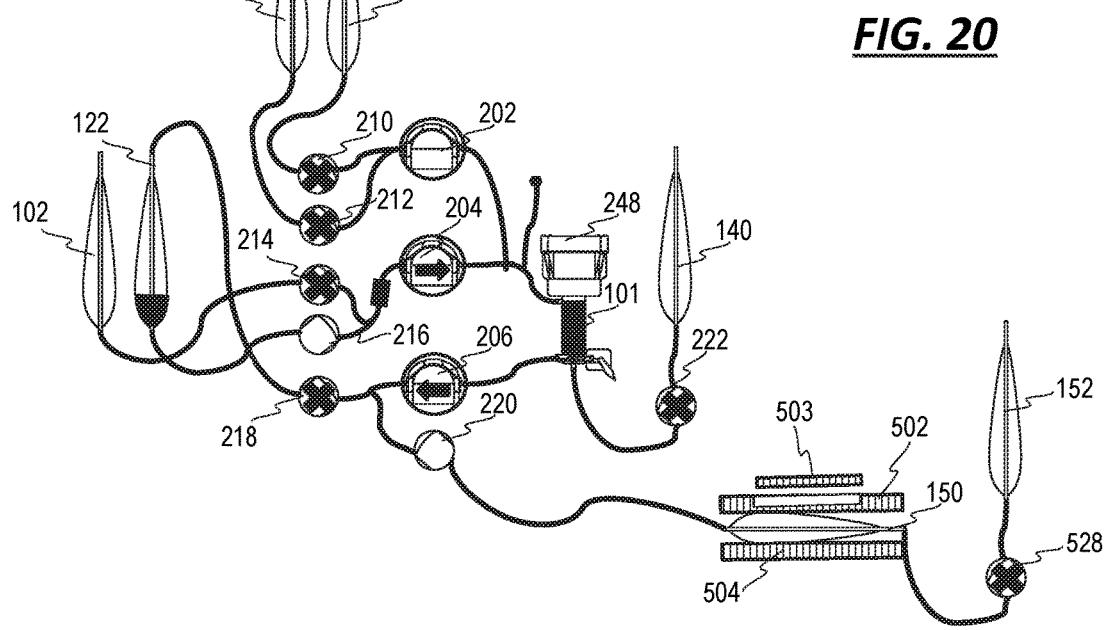
Figure 22:
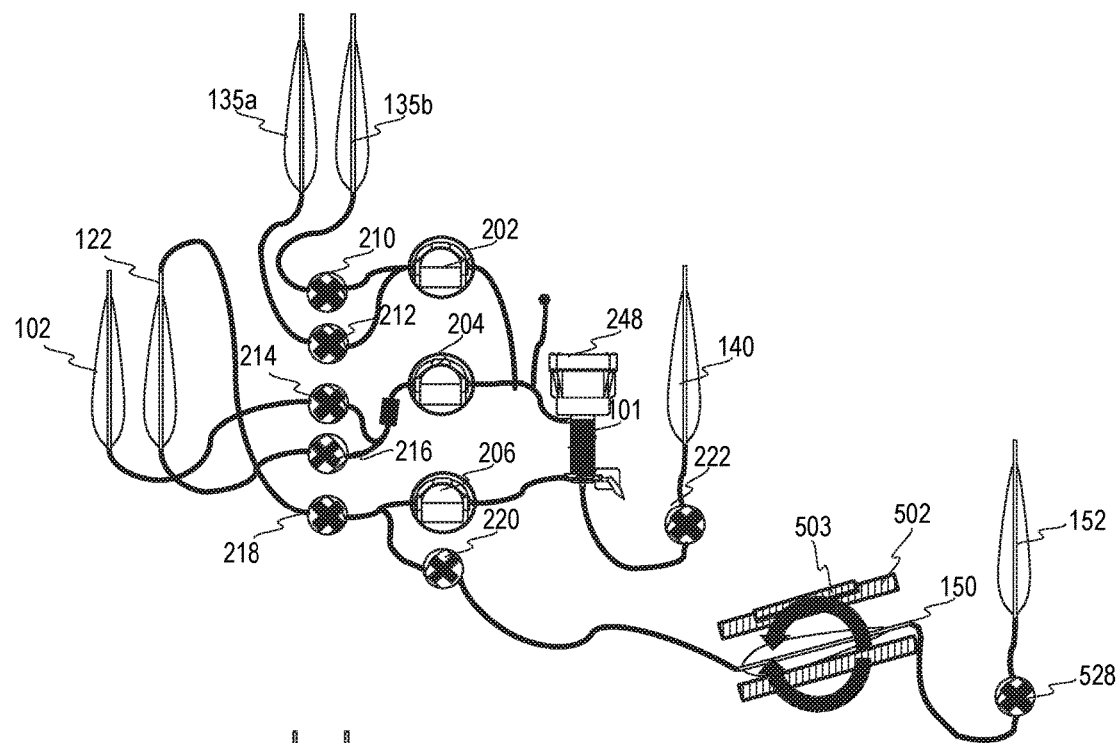
Figure 23:
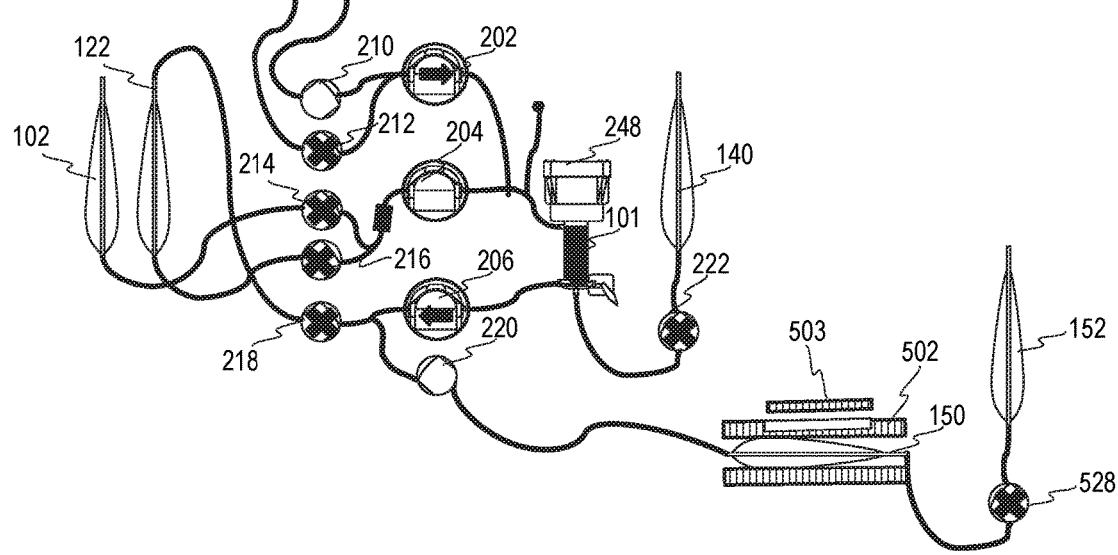
Figure 24:
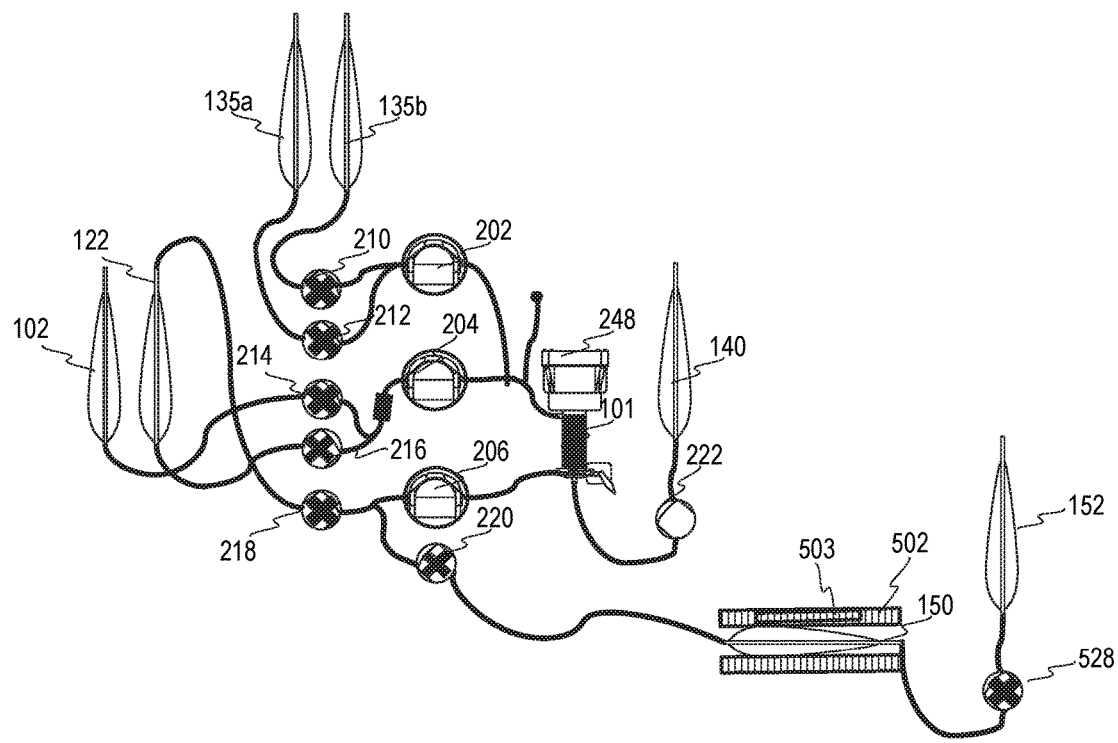
Figure 25:
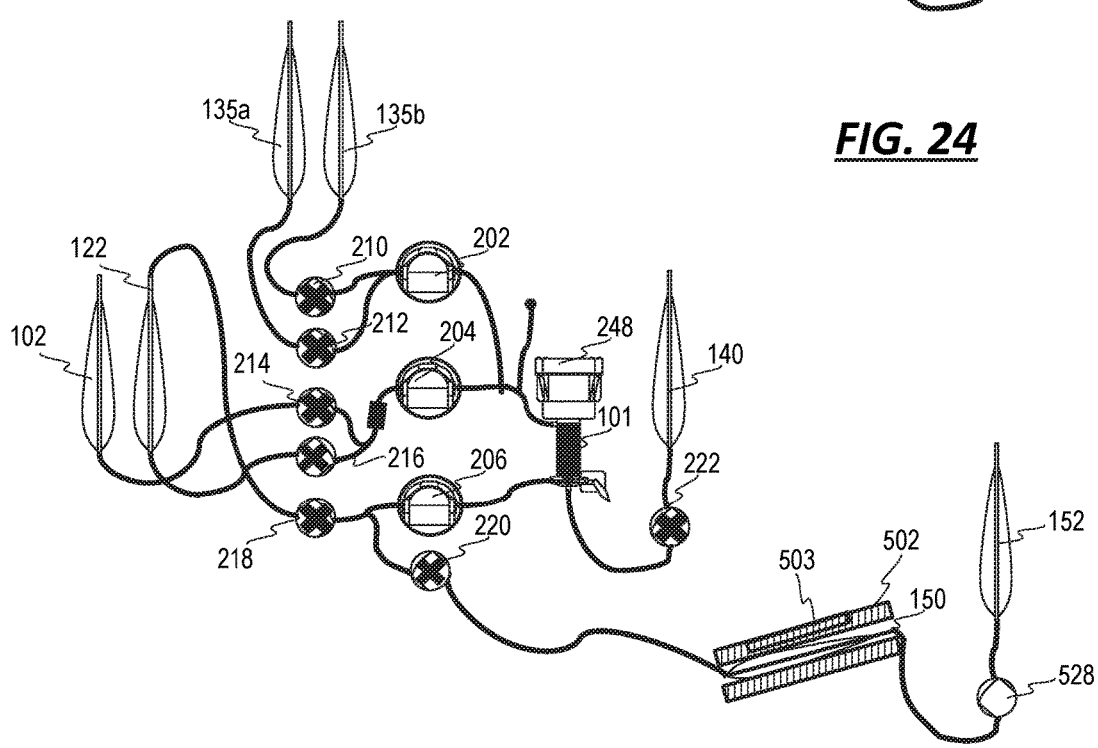
Figure 26:
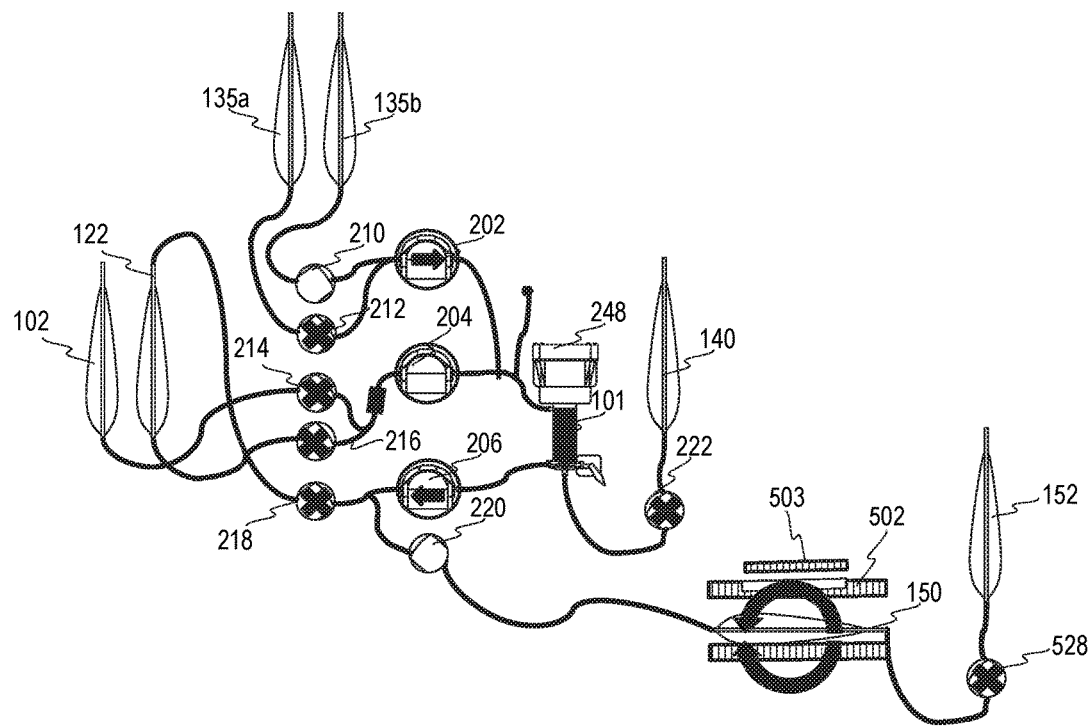
Figure 27:
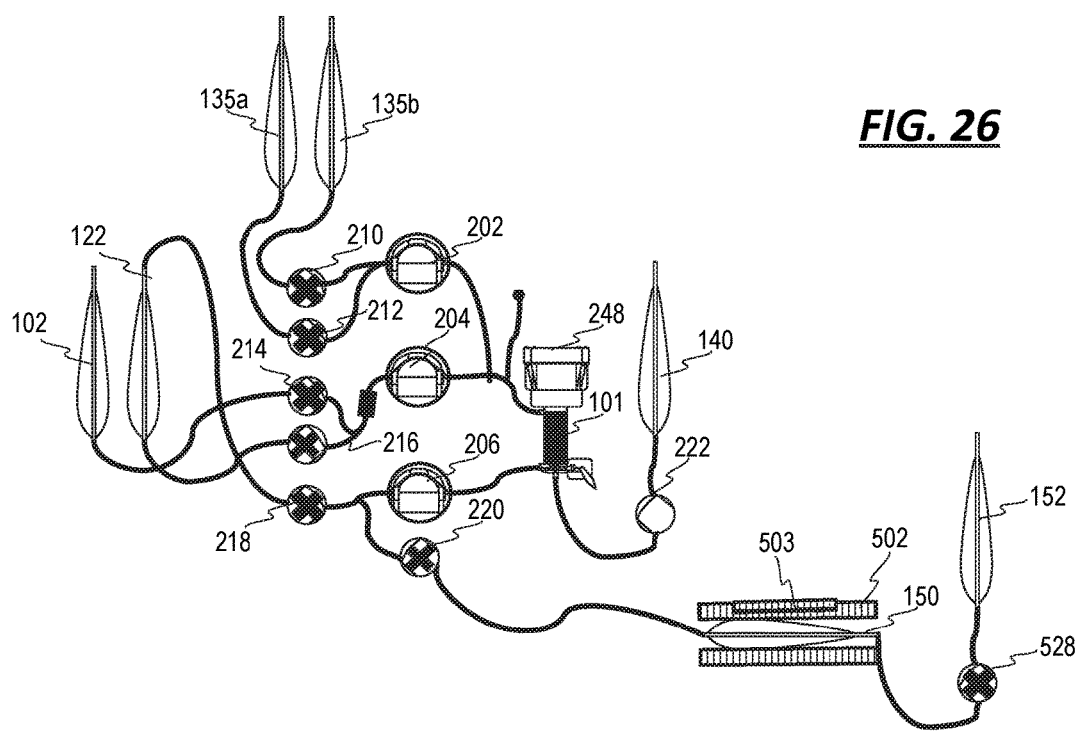
Figure 28:
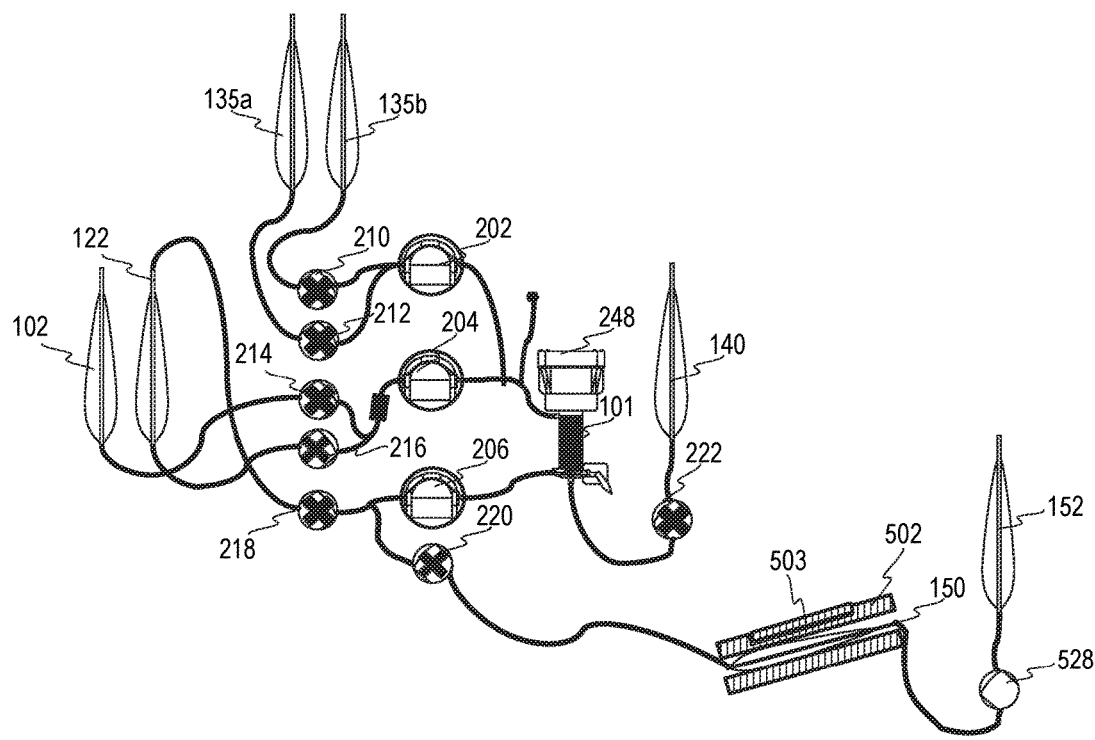
Figure 29:
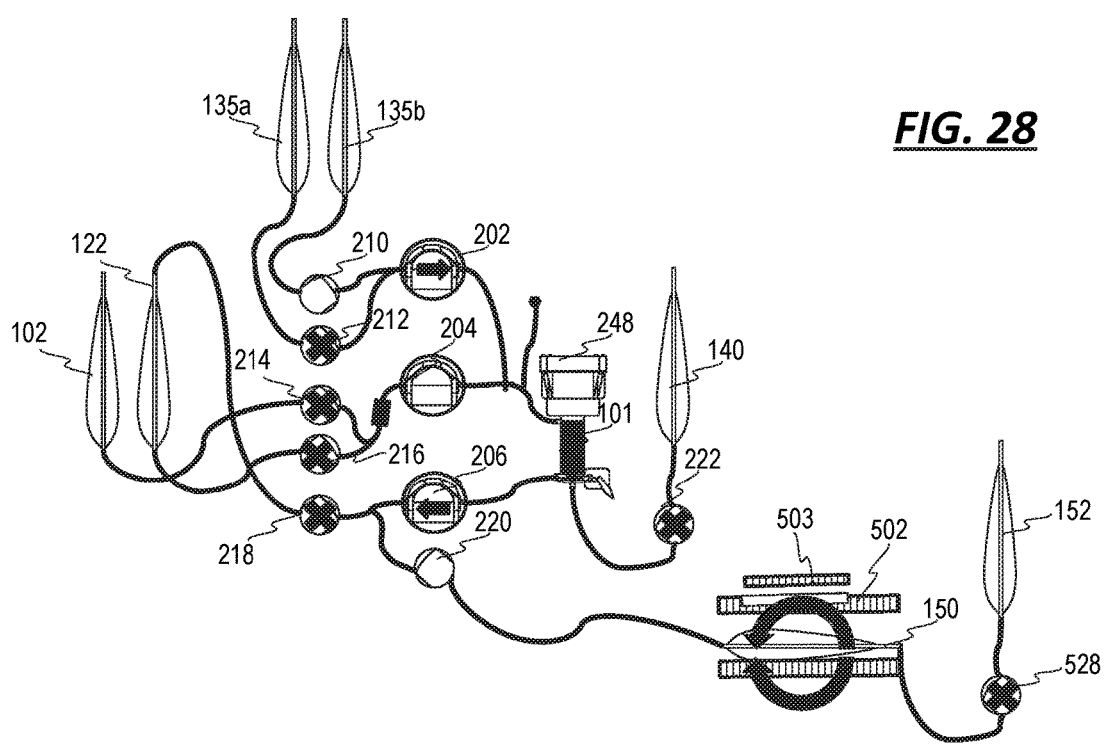

A specific embodiment of a method 400 of operating the apparatus 200 is provided in FIG. 7, with particular operational states of the processor 100, 200 and separator 500 illustrated in FIGS. 8-29. According to this embodiment, the method 400 of operating the apparatus 200 includes several steps, and some of the steps may be grouped or organized into one or more cycles. For example, reduction, rinse and dilution steps 404, 406, 408 may define a cycle, which cycle may be repeated several times to define a multi-cycle procedure; the fact that a single cycle is illustrated does not exclude the possibility that additional cycles may be performed. Further, it will be recognized that an apparatus 200 need not perform every step illustrated in FIG. 7, but an apparatus 200 may operate as illustrated in FIG. 7 according to this disclosure.

To begin, the controller 300 may cause the apparatus 200 to perform the step of priming at block 402. According to this step, wash media from one or both of the wash media containers 135a, 135b is transferred to the disposable set 100. In fact, a small amount of wash media may be transferred to each of the other containers 102, 122, 140 to ensure that the containers 102, 122, 140 are connected. To this end, the controller 300 may cause clamps 210, 212, 214, 216, 218, 222 to open to permit the transfer of fluid to the containers 102, 122, 140.

As part of this priming action, the controller 300 first may operate the magnetic separator 500 to evacuate the container 150 by moving the plates 502, 504 toward each other (with the magnet 503 disengaged) to force or express the air from the container 150 into the set 100 (e.g., into the container 122) with the plates 502, 504 arranged relatively horizontally. Compare FIG. 8 with FIG. 9. With the plates 502, 504 moved toward each other and the container 150 compressed between them, the controller 300 then may open clamps 210, 220 and operate pumps 202, 206 to move fluid from the wash container 135b into the lines that connect with the container 150. See FIG. 10. According to certain embodiments, the controller 300 also may operate the separator 500 to space the plates 502, 504 so that some fluid flowing along the lines that connect with the container 150 passes into the container 150 as well. If this occurs, once the desired volume or amount of fluid has been transferred to container 150, the clamps 210, 220 may be closed, and the inclination of the plates 502, 504 adjusted such that the end of the container 150 attached to the container 152 is elevated relative to the end of the container 150 that is attached to the remainder of the circuit 100. See FIG. 11. The clamp 528 may be opened, and the plates 502, 504 moved toward each other (with the magnet 503 disengaged) so as to compress the container 150 between them to force or express the fluid (e.g., air, prime solution) from the container 150 into container 152. When this action is completed, the clamp 528 is again closed.

The method 400 continues to block 404, where the controller 300 causes the apparatus 200 to perform a reduction. See FIG. 12. The controller 300 causes the biological fluid from the source container 102 (and optionally wash media from the wash media container(s) 135a, 135b) to be transferred to the separator 101. For example, the controller 300 may open clamp 214 and operate pump 204 to transfer the fluids from the container 102 to the separator 101. The separator 101 (in conjunction with operation of the drive 248 by controller 300) produces two streams: a first, or retentate, stream that is directed into the in-process container 122, and a second, or filtrate, stream that is directed into the waste container 140. For example, the controller 300 may open clamp 218 and operate pump 206 to cause flow into the in-process container 122 (clamp 220 being closed), and may open clamp 222 to permit flow into the container 140. As a consequence, plasma and platelets are removed from the biological fluid, and white blood cells are transferred to the in-process container 122.

To facilitate the separation of the plasma and platelets from the white blood cells within the biological fluid, the membrane of the separator 101 may be a thin sheet (10-50 μm in thickness) of polycarbonate with pore sizes of approximately 4 μm, by way of example and not by way of limitation. The pore size is selected to allow platelets (which may be 2-4 μm in size) to pass through, abut not the target cells.

After the step of block 404 is complete, the controller 300 causes wash media to be passed through the set 100 (i.e., the set is rinsed) and the media is added to the in-process bag 122 at block 406. This may be achieved, for example, by closing clamps 214, 222, while opening clamps 210 (and/or 212), 216, 218 and operating pumps 202, 204, 206 as illustrated. See FIG. 13. After block 406, the method 400 proceeds to block 408, where the controller 300 may cause additional wash media to be added to the in-process bag 122, if required. As mentioned above, the actions of blocks 404-408 may be repeated as additional cycles, as may be required, before the method 400 continues to block 410. When block 408 is complete, the method 400 may continue with block 410 to start the process of associating magnetic particles with the target cells.

At block 410, all of the clamps 210, 212, 214, 216, 218, 220, 222 are closed. See FIG. 14. According to one embodiment, the processor 100, 200 may automatically pause at this point, so that the operator can manually inject a monoclonal antibody (mAb) solution into the in-process container 122; for example, an introducer container may be attached to the in-process container 122 either prior to the procedure or in a sterile manner during the procedure and the solution is injected into the in-process container 122 from the introducer container. According to other embodiments, the monoclonal antibody is introduced automatically into the in-process container 122. The method 400 may then proceed to block 412, where the contents of the container 122 may be permitted to remain in the container 122 for a period of time to allow for interaction between the monoclonal antibodies and the target cells. As part of the incubation step at block 412, the clamps 216, 218 may be opened and pumps 204, 206 and drive 248 may be operated to mix the suspension in the container 122 to improve the interaction between the monoclonal antibodies and target cells. See FIG. 15. For example, the spinning membrane 101 may be operated at a speed of between 500-700 rpm. Transfer of fluid from one or both of the wash solution containers 135a, 135b may occur at this time to optimize the volume for incubation. According to one embodiment, the total incubation time (including time spent mixing the contents of the in-process container 122) may be thirty minutes, while the incubation temperature may be room temperature.

Continuing at block 414, the apparatus 200 may be operated to remove excess, unassociated or unbound mAb from the contents of the container 122. To achieve this, the clamps 216, 218, 222 are opened and pumps 204, 206 and drive 248 are operated, with the target cells and bound mAb being returned to the container 122 and the unbound mAb being transferred to the container 140. The clamp 210 may also be opened and pump 202 operated to introduce wash solution at the same time. See FIG. 16. The clamp 222 may be closed while the clamp 210 is open and the pump 202 operated to rinse any remaining target cells bound to mAb into the container 122 at block 416. See FIG. 17.

It should be mentioned that the exemplary membrane of the separator 101 described above, a thin sheet (10-50 µm in thickness) of polycarbonate with pore sizes of approximately 4 µm, also should sufficient function to remove the monoclonal antibodies from the target cells with associated monoclonal antibodies. In particular, the monoclonal antibodies may have a size of approximately 50 nm, such that the pore size provided above should be suitable.

At block 418, all of the clamps 210, 212, 214, 216, 218, 220, 222 are again closed. See FIG. 18. According to one embodiment, the processor 100, 200 may automatically pause at this point, so that the operator can manually inject a ferrofluid (FF) into the in-process container 122; for example, an introducer container may be attached to the in-process container 122 either prior to the procedure or in a sterile manner during the procedure and the ferrofluid is injected into the in-process container 122 from the introducer container. According to other embodiments, the ferrofluid is introduced automatically into the in-process container 122. The method 400 may then proceed to block 420, where the contents of the container 122 may be permitted to remain in the container 122 for a period of time to allow for interaction between the monoclonal antibodies and the magnetic particles (e.g., beads) in the ferrofluid. As part of the incubation step at block 420, the clamps 216, 218 may be opened and pumps 204, 206 and drive 248 may be operated to mix the suspension in the container 122 to improve the interaction between the monoclonal antibodies and magnetic particles. See FIG. 19. Transfer of fluid from one or both of the wash solution containers 135a, 135b may occur at this time to optimize the volume for incubation.

Continuing an optional block 422, the apparatus 200 may be operated to remove excess or unbound magnetic particles from the contents of the container 122. To achieve this, the clamps 216, 218, 222 are opened and pumps 204, 206 and drive 248 are operated, with the target cells and bound magnetic particles being returned to the container 122 and the unbound magnetic particles being transferred to the container 140. See FIG. 20. The clamp 210 may also be opened and pump 202 operated to introduce wash solution at the same time.

To begin the magnetic separation or selection of the target cells, the contents of the in-process container 122 are transferred at block 424 from the container 122 to the container 150 that is disposed at the magnetic separator 500, and in particular between the plates 502, 504. To achieve this, clamps 216, 220 are opened and pumps 204, 206 are operated. See FIG. 21. Once this complete and clamps 216, 220 are closed, the method 400 continues to block 426, and the magnet 503 associated with plate 502 is engaged with the plate 502 and activated (if necessary), causing the target cells associated with the magnetic particles and any unbound magnetic particles to migrate to a portion of the container, in particular the portion of the container adjacent the magnet 503.

At block 428, the contents of the container 150 are permitted to remain in container 150 for a period of time (e.g., 30 seconds) with the magnet 503 engaged and activated. The method may continue to block 430, where the plate (or frame) 502 and magnet 503 are disengaged from the container 150, and the contents of the container 150 are agitated at block 432. See FIG. 22. For example, the plates 502, 504 may be alternatively inclined back and forth between a position where the first end 524 is higher than the second end 526 and a position where the second end 526 is higher than the first end 524. The actions of blocks 426-432 may be repeated as several cycles over a longer period of time (e.g., several minutes). Once this portion of the method 400 is complete, the method 400 continues to block 434, and the magnet 403 is disengaged from the plate 502. See FIG. 23.

At block 436, fluid is added to the container 150 from one of the wash containers 135a, 135b. See also FIG. 23. To permit this, the spacing between the plates 502, 504 may be increased. In addition, the clamps 210, 220 may be opened and pumps 202, 206 operated to move fluid from the container 135a to the container 150. Once the desired volume is achieved in the container 150, the magnet 503 is engaged with the plate 502 at block 438 and the contents of the container 150 are incubated for a period of time at block 440. See FIG. 24. The method 400 then continues to block 442 for removal of the negative fraction.

According to the embodiment illustrated, the plates 502, 504 are pivoted or tilted about the axle 520 at block 442 such that the end connected to the remainder of the circuit 100 is at a lower elevation than the end attached to the container 152. See FIG. 25. The clamp 528 is opened and the plates 502, 504 moved toward each other so that the container 150 compressed between them to force or express the fluid from the container 150 to the container 152. For example, the plates 502, 504 may be moved toward each other until the volume in the container 150 is approximately 1 ml. By using the container 150 as a flow-through container (through the inclusion of the container 152 attached to the container 150), the negative fractions are not transported along the same line as solution enters the container 150. This limits the possibility of the negative fractions being carried back into the container 150 upon subsequent transfer of fluid to the container 150 through the line that connects the container 150 to the remainder of the circuit 100.

The method 400 then proceeds to block 444 where the container 150 is rinsed to attempt to remove any cells that are not target cells associated with magnetic particles. To this end, the clamps 210, 220 are opened and pumps 202, 206 operated to move fluid (e.g., wash solution) from container 135b to the container 150. See FIG. 26. At the same time or shortly thereafter, the plate 502 and the magnet 503 are disengaged from the container 150 at block 446, and the container 150 may be agitated at block 448, by changing the inclination of the plates 502, 504 back and forth.

The plate 502 and the magnet 503 may be re-engaged at block 450 and the contents of the container incubated at block 452. See FIG. 27. The method 400 may continue to block 454 where the rinse solution is expressed from the container 150. Again, the plates 502, 504 are pivoted or tilted about the axle 520 such that the end connected to the remainder of the circuit 100 is at a lower elevation than the end attached to the container 152. See FIG. 28. The clamp 528 is opened and the plates 502, 504 moved toward each other so that the container 150 compressed between them to force or express the fluid from the container 150 to the container 152. For example, the plates 502, 504 may be moved toward each other until the volume in the container 150 is approximately 1 ml.

The actions of blocks 444-454 may be repeated for several cycles, as may be desired. The container 152 also may be replaced while the clamp 528 is closed during the action of block 444. Once the desired number of cycles of blocks 444-452 have been completed, the method 400 continues to block 456.

At block 456, the plate 502 and magnet 503 are disengaged from the container 150. See FIG. 29. At block 458, the volume of the container 150 is brought to its final amount by closing clamp 528, opening clamps 210, 220, and operating pumps 202, 206 to transfer fluid from the container 135b to the container 150. The container 150 may also be agitated at block 460 by varying the inclination of the container 150 either at the same time as fluid is transferred to the container 150 or shortly thereafter.

The container 150 and/or container 152 may then be sealed and removed from the remainder of the circuit 100. According to certain embodiments, the positive fraction magnetically selected and retained in the container 150 may be the desired product. According to other embodiments, the negative faction transferred to the container 152 may be (or may also be) a desired product, and so the container 152 may be sealed and detached after block 442 and replaced with another container before the rinse cycle(s) of blocks 444-454.

Thus, an improved method and system have been disclosed for the processing of biological cells. The description provided above is intended for illustrative purposes only and is not intended to limit the scope of the invention to any specific method, system, or apparatus, or device described herein except as may be explicitly delineated above.

Other Aspects

Aspect 1. A cell processing system comprising:
a first processor connectable to a source container filled with a biological fluid, the first processor comprising:
  a separator configured to separate the biological fluid from the source container into at least two streams of material; and
  a first container configured to receive one of the at least two streams along a first fluid pathway;
a second processor connectable to the first container, the second processor comprising:
  a magnetic separator configured to select target cells, the target cells being associated with magnetic particles;
  a second, pass-through container associated with the magnetic separator, the second container connected at a first end to the first container along a second fluid pathway; and
  a third container connected to a second end of the pass-through container; and
one of the first processor and the second processor comprising at least one pump configured to transfer material between the separator and the first container along the first fluid pathway, and between the first container and the second container along the second fluid pathway; and
at least one controller coupled to the first processor and the second processor.

Aspect 2. The cell processing system according to aspect 1, wherein a closed fluid circuit defines in part the first and second processors, the closed fluid circuit comprising and connecting the first, second and third containers.

Aspect 3. The cell processing system according to aspect 1 or 2, wherein the magnetic separator comprises first and second opposing plates,
  at least the first plate translatable relative to the second plate,
  the second container disposed between the first and second plates, and
  the first plate comprising a magnet.

Aspect 4. The cell processing system according to aspect 3, wherein the at least one controller is configured to move the first and second plates toward each other to express fluid from the second container into the third container.

Aspect 5. The cell processing system according to aspect 3 or 4, wherein the first and second plates are mounted on an axle, the first and second plates being pivotable about the axle to change the inclination of the first and second plates and the second container disposed between the first and second plates.

Aspect 6. The cell processing system according to any one of aspects 3-5, wherein the magnet is translatable relative to the first plate.

Aspect 7. The cell processing system according to aspect according to any one of the preceding aspects, wherein the at least one controller is configured to operate the first processor to associate the target cells with the magnetic particles in the first container, to operate the at least one pump to move the target cells with associated magnetic particles to the magnetic separator, and to operate the magnetic separator to select the target cells.

Aspect 8. The cell processing system according to aspect 7, wherein the at least one controller comprises a processor and the processor is programmed to operate the first processor to associate the target cells with the magnetic particles in the first container, to operate the at least one pump to move the target cells with associated magnetic particles to the magnetic separator, and to operate the magnetic separator to select the target cells.

Aspect 9. The cell processing system according to any one of the preceding aspects, wherein the at least one controller is configured to operate the at least one pump to circulate the target cells and the magnetic particles between the first container and the separator during association of the target cells with the magnetic particles.

Aspect 10. The cell processing system according to any one of the preceding aspects, wherein the separator of the first processor comprises a spinning membrane separator.

Aspect 11. A cell processing method comprising:
separating a biological fluid into at least two streams, one of the streams including target cells;
associating magnetic particles with the target cells;
transporting the target cells with associated magnetic particles to a pass-through container via a port at a first end of the pass-through container;
selecting the target cells in the pass-through container using a magnetic field; and transporting non-selected materials from the pass-through container via a port at a second end of the pass-through container opposite the first end.

Aspect 12. The cell processing method according to aspect 11, wherein transporting the non-selected materials from the pass-through container comprises compressing the pass-through container to express the non-selected materials from the pass-through container.

Aspect 13. The cell processing method according to aspect 11 or 12, selecting the target cells using a magnetic field comprises disposing a magnet adjacent the target cells associated with magnetic particles.

Aspect 14. The cell processing method according to aspect 13, wherein the target cells associated with magnetic particles are disposed in a container that is disposed between two moveable plates, one of the plates comprising a magnet that is translatable relative to the container.

Aspect 15. The cell processing method according to aspect 14, wherein transporting the non-selected materials from the pass-through container comprises moving the two moveable plates toward each other to express the non-selected materials from the pass-through container.

Aspect 16. The cell processing method according to any one of aspects 11-15, wherein separating the biological fluid comprises separating the biological fluid into a first fraction comprising at least white blood cells and a second fraction comprising at least platelets, the target cells comprising the white blood cells.

Aspect 17. The cell processing method according to aspect 16, wherein separating the biological fluid into at least two streams comprises passing the biological fluid through a spinning membrane separator.

Aspect 18. The cell processing method according to any one of aspects 11-17, wherein associating magnetic particles with the target cells comprises associating monoclonal antibodies with the target cells, and associating magnetic particles with the monoclonal antibodies associated with the target cells.

Aspect 19. The cell processing method according to aspect 18, wherein:
associating monoclonal antibodies with the target cells comprises adding the monoclonal antibodies to the target cells in a container and subsequently passing the contents of the container through a spinning membrane separator to mix the contents of the container; and attaching magnetic particles with the monoclonal antibodies comprises adding the magnetic particles to the monoclonal antibodies associated with the target cells in the container and subsequently passing the contents of the container through a spinning membrane separator to mix the contents of the container.

Aspect 20. The cell processing method according to any one of aspects 11-19, wherein the method is performed within a single closed fluid circuit.

The invention claimed is:

1. A cell processing system comprising:
a first processor connectable to a source container filled with a biological fluid, the first processor comprising:
a separator configured to separate the biological fluid from the source container into at least two streams of material; and
a first container configured to receive one of the at least two streams along a first fluid pathway;
a second processor connectable to the first container, the second processor comprising:
a magnetic separator configured to select target cells, the target cells being associated with magnetic particles;
a second, pass-through container associated with the magnetic separator, the second, pass-through container connected at a first end to the first container along a second fluid pathway; and
a third container connected to a second end of the second, pass-through container; and
one of the first processor and the second processor comprising at least one pump configured to transfer material between the separator and the first container along the first fluid pathway, and between the first container and the second, pass-through container along the second fluid pathway; and
at least one controller coupled to the first processor and the second processor;
wherein the magnetic separator comprises first and second opposing plates, at least the first plate translatable relative to the second plate, the second, pass-through container disposed between the first and second plates, and the first plate comprising a magnet,
wherein the at least one controller is configured to move the first and second plates toward each other to express fluid from the second, pass-through container into the third container.

2. The cell processing system according to claim 1, wherein a closed fluid circuit defines in part the first and second processors, the closed fluid circuit comprising and connecting the first, second and third containers.

3. The cell processing system according to claim 1, wherein the first and second plates are mounted on an axle, the first and second plates being pivotable about the axle to change the inclination of the first and second plates and the second container disposed between the first and second plates.

4. The cell processing system according to claim 1, wherein the magnet is translatable relative to the first plate.

5. The cell processing system according to claim 1, wherein the at least one controller is configured to operate the first processor to associate the target cells with the magnetic particles in the first container, to operate the at least one pump to move the target cells with associated magnetic particles to the magnetic separator, and to operate the magnetic separator to select the target cells.

6. The cell processing system according to claim 5, wherein the at least one controller comprises a processor and the processor is programmed to operate the first processor to associate the target cells with the magnetic particles in the first container, to operate the at least one pump to move the target cells with associated magnetic particles to the magnetic separator, and to operate the magnetic separator to select the target cells.

7. The cell processing system according to claim 1, wherein the at least one controller is configured to operate the at least one pump to circulate the target cells and the magnetic particles between the first container and the separator during association of the target cells with the magnetic particles.

8. The cell processing system according to claim 1, wherein the separator of the first processor comprises a spinning membrane separator.

* * * * *